US006895305B2

(12) United States Patent
Lathan et al.

(10) Patent No.: US 6,895,305 B2
(45) Date of Patent: May 17, 2005

(54) ROBOTIC APPARATUS AND WIRELESS COMMUNICATION SYSTEM

(75) Inventors: Corinna E. Lathan, Wheaton, MD (US); Michael R. Tracey, Hillsborough, NJ (US); Jack M. Vice, Glenndale, MD (US); Allison Druin, Hyattsville, MD (US); Catherine Plaisant, University Park, MD (US)

(73) Assignees: Anthrotronix, Inc., Silver Spring, MD (US); University of Maryland, College Park Riverdale, MD (US)

(*) Notice: Subject to any disclaimer, the term of this patent is extended or adjusted under 35 U.S.C. 154(b) by 0 days.

(21) Appl. No.: 10/085,821

(22) Filed: Feb. 27, 2002

(65) Prior Publication Data

US 2002/0120362 A1 Aug. 29, 2002

Related U.S. Application Data

(60) Provisional application No. 60/271,765, filed on Feb. 27, 2001.

(51) Int. Cl.[7] .............................................. G06F 19/00
(52) U.S. Cl. ....................... 700/245; 700/131; 700/132; 700/258; 600/101; 600/424; 600/427; 600/595; 606/130; 219/130.21; 128/97
(58) Field of Search ................... 700/131, 132, 700/245, 258; 600/101, 424, 427, 595; 606/130; 128/897; 219/130.21

(56) References Cited

U.S. PATENT DOCUMENTS

| 4,556,216 | A | | 12/1985 | Pitkanen ..................... 482/131 |
|---|---|---|---|---|
| 4,571,682 | A | | 2/1986 | Silverman et al. .......... 600/301 |
| 5,466,213 | A | | 11/1995 | Hogan et al. ................ 601/33 |
| 5,963,712 | A | | 10/1999 | Fujita et al. ................. 395/99 |
| 6,058,385 | A | | 5/2000 | Koza et al. .................. 706/13 |
| 6,084,205 | A | * | 7/2000 | Sheaffer et al. ......... 219/130.21 |
| 6,275,773 | B1 | | 8/2001 | Lemelson et al. .......... 701/301 |
| 6,321,140 | B1 | | 11/2001 | Fujita et al. ................. 700/248 |
| 6,511,442 | B1 | * | 1/2003 | Lathan et al. ................ 600/595 |

FOREIGN PATENT DOCUMENTS

WO          0107112          2/2001

OTHER PUBLICATIONS

Osadciw et al., Improving personal identification accuracy using multisensor fusion for building access control applications, 2002, IEEE, pp. 1176–1183.*

Hamann, Chip cards—The applicaion revolusion, 1997, IEEE, pp. 1.3.1–1.3.8.*

Mack, Minimally Invasive and Robotics Surgery, 2001, IEEE, pp. 568–572.*

Hara et al., Real–Time Facial Interaction Between Human and 3D Face Robot Agent, 1996, IEEE/Internet, pp. 401–409.

* cited by examiner

*Primary Examiner*—Thomas G. Black
*Assistant Examiner*—McDieunel Marc
(74) *Attorney, Agent, or Firm*—Lieberman & Brandsdorfer, LLC

(57) ABSTRACT

A robotic apparatus and system adapted to communicate with a wireless sensor. The apparatus may be either physical or virtual in nature and is adapted to communicate physical movements with a wireless sensor. Data received from the sensor and/or robotic apparatus may be reviewed in a real-time mode, or may be saved for review at a later time. In addition, the apparatus may be controlled through an operator that is in local or remote communication with the apparatus. The robotic system may include pre-programmed interactive platforms for enabling communication between a user and the apparatus in a dynamic mode. In addition, the system may allow an operator to program a game/story for use as an interactive platform. Accordingly, the apparatus and system provides a platform for rehabilitative exercise of a patient as well as an entertainment device.

54 Claims, 36 Drawing Sheets

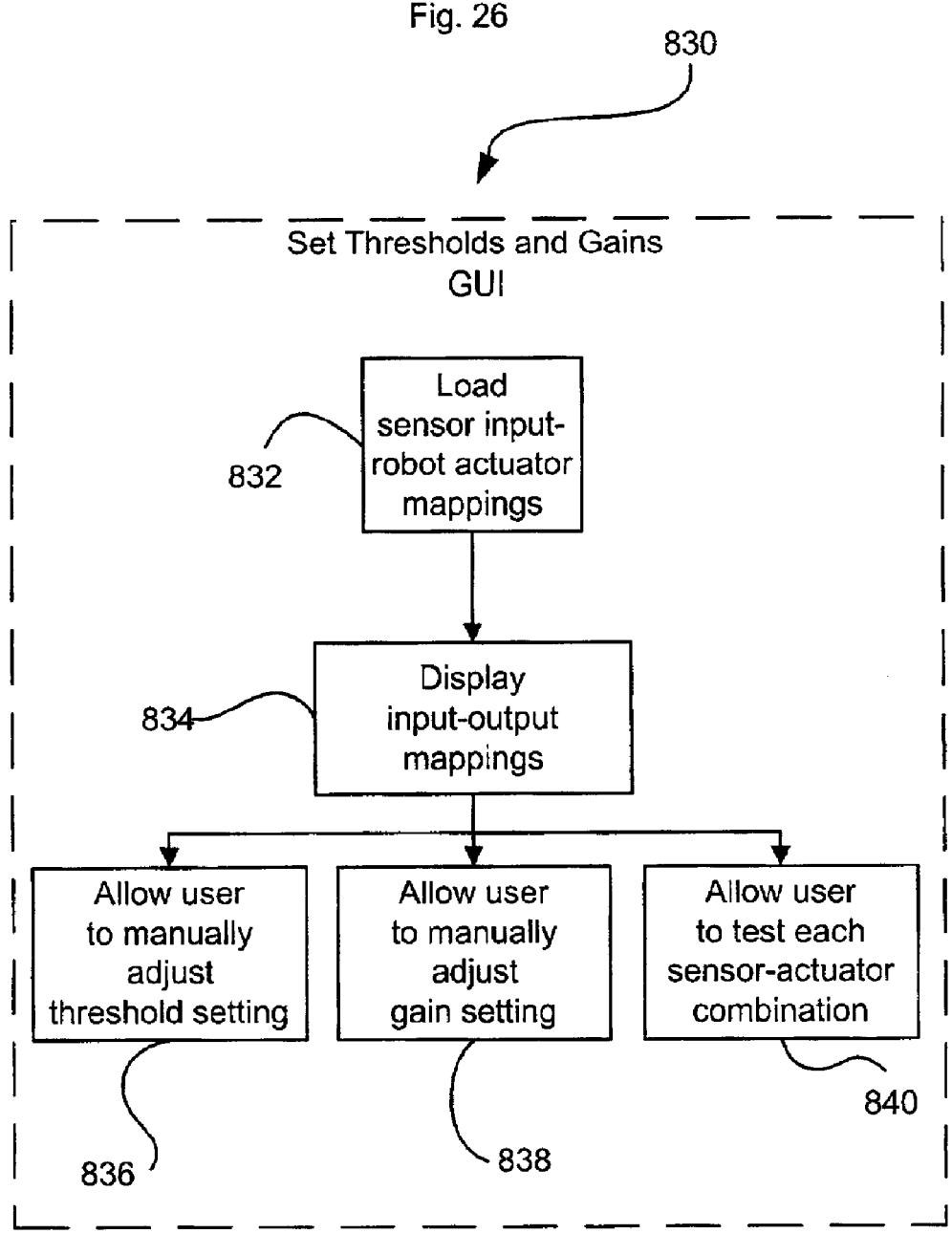

ROBOTIC APPARATUS AND WIRELESS COMMUNICATION SYSTEM

CROSS REFERENCE TO RELATED APPLICATION(S)

This is a non-provisional utility patent application claiming benefit of the filing date of U.S. provisional application Ser. No. 60/271,765 filed Feb. 27, 2001, and titled INTERACTIVE ELECTRONIC SYSTEM.

BACKGROUND OF THE INVENTION

1. Technical Field

This invention relates to a robotic apparatus and wireless communication system. More specifically, the invention relates to an apparatus for enabling remote communication between a sensor and an actuator in communication with the robot.

2. Description of the Prior Art

Rehabilitation therapy is generally categorized into physical, speech-language, and/or occupational therapy. These forms of therapy are generally conducted for persons recovering from injuries, or persons subject to chronic illness and/or disabilities. Healthcare professionals recognize that proper rehabilitative therapy may significantly reduce further injury and may aid in the promotion of wellness and recovery.

There are many different forms of rehabilitative therapies. Finding the proper therapy for each individual is dependent upon the circumstances affecting their disability and/or injury. Part of ascertaining a proper rehabilitative program is to evaluate an individual's capabilities in view of any existing impairments, whether chronic or temporary. However, another consideration in the evaluation is the ability to maintain a proper level of patient motivation with the selected therapy, or to enable the therapy to be altered to maintain a proper level of patient motivation.

One form of technology associated with a rehabilitation apparatus and system is biofeedback. This is a treatment technique for patients who have a loss of perception of some body function. A biofeedback apparatus monitors the specific body function for which the patient has suffered a loss of perception and provides patients with a visual or auditory signal in response to a change in the particular body function. A form of biofeedback is an electromyographic (EMG) biofeedback apparatus and system. An EMG system aims to teach patients how to use muscles which are in need of rehabilitation. EMG systems generally provide feedback to the patient in the form of visual and/or audio signals. Recent developments in EMG biofeedback apparatus include sensors in communication with specific body parts participating in the exercise as shown in U.S. patent application Ser. No. 09/361,753, now U.S. Pat. No. 6,413,190, assigned to Enhanced Mobility Technologies. In this application, the sensors themselves are in communication with a computer to record and assess the progress of the patient. Accordingly, EMG apparatus and systems have progressed to a point where they may include an evaluation tool to determine the progress of the patient in view of the rehabilitation exercises conducted.

However, EMG devices are merely biofeedback devices to indicate a specific area of a patient's body is being subject to an exercise. EMG devices do not encompass an interactive component with the patient to motivate the patient in maintaining the specified exercise. Accordingly, what is desirable is an interactive apparatus that provides biofeedback and maintains the attention and focus of the patient on the apparatus.

SUMMARY OF THE INVENTION

This invention comprises a robotic apparatus controlled via wireless sensors or a console to provide feedback to a user of the apparatus in the form of visual movement of said apparatus or through dynamic interaction.

A first aspect of the invention is a robotic apparatus comprising a controller adapted to process a signal to an actuator. The apparatus includes a dynamic feedback control system between a user and the robotic apparatus. The control system includes a sensor in communication with a user. The sensor senses input of the user and communicates the sensor signal with the robot. The actuator of the robot is adapted to receive the signal and to actuate a part of the robot in response to the user input when the user input exceeds a threshold. The user input may be physical such as body movement or voice. The sensor and actuator are in wireless communication. Furthermore, the sensor may be secured to a user or secured to a console remote from both the user and the actuator of the robot. The apparatus may also include a computer to store sensor data. The computer may be internal to the robot, internal to the sensor, or external from the robot. The apparatus may also include an operator interface to modify configuration of the robot, to select an interactive mode of operation between the, robot and the user, and to allow an operator to evaluate user input. In addition, the operator interface may enable the operator to program a unique interactive mode of operation of the robot and the user. The operator interface may be accessible from a location remote from the robot and the user. The robot may be a physical apparatus, or it may be virtual.

A second aspect of the invention is a method for controlling a robotic apparatus. The method includes the steps of reading a sensor data in communication with the robot, processing sensor data, transmitting the sensor data over a wireless connection from the sensor to a receiver in communication with the robot, parsing the sensor data, activating an actuator of the robot in response to the parsed data, and interacting with the apparatus in a dynamic feedback control system. The step of processing the sensor data may include processing physical input signals from the sensor being monitored and may include functions selected from the group consisting of: analog to digital converting, compressing, mapping, thresholding, filtering, or pattern recognition. The method may include the step of directly transmitting the sensor data to the robot for controlling the actuator of the robot in real-time. The step of parsing the data may include functions selected from the group consisting of: analog to digital converting, de-compressing, de-crypting, mapping, thresholding, filtering, or pattern recognition. In addition, the method may include recording the sensor data for review at a subsequent time, or to play the sensor data at a subsequent time with the robotic apparatus. The recorded data may be accessed from a remote location for evaluation purposes, or to play the data in conjunction with the robotic apparatus. The method may also include providing interactive communication between the sensor and the robot. In addition, the method may also enable the configuration of the robot to be modified through an operator interface, either locally or remotely through a networked computer in communication with the robot or a remote console.

A third aspect of the invention is an article comprising a computer-readable signal-bearing medium. The medium includes means for sending data over a wireless connection, means for communicating activation of a signal in a remote robotic apparatus, means for remotely setting configuration parameters of a sensor and an actuator of the robotic apparatus, and means for providing dynamic interaction between the robotic apparatus and a user in communication with the robotic apparatus. The means may be selected from a recordable data storage medium or a modulated carrier signal, or a combination thereof. The means for communicating activation of a signal may be a communication protocol. The means for remotely setting configuration parameters may include a graphical user interface. In addition, the article may also include the process of conducting real-time assessment of signal data, as well as remote interaction between an operator and the robotic apparatus in real-time. The actuator activation data may be saved and recorded in the medium. The saved data may then be transmitted in the medium to a computer remote from the robotic apparatus.

A fourth aspect of the invention is a signal communication system. The system includes a wireless sensor in communication with an actuator, a power control module, a transceiver, a central processing unit, and a dynamic control system between the sensor and the actuator. The control system is adapted to enable control of the actuator in response to feedback communicated to the sensor. The central processing unit and transceiver may be adapted to receive and process sensor data and to transmit the data to the actuator. The system preferably includes a plurality of wireless sensors in communication with a single central processing unit. The physical sensors may be physically connected. In addition, the system may include multiple processing units with each unit having a plurality of connected sensors.

Other features and advantages of this invention will become apparent from the following detailed description of the presently preferred embodiment of the invention, taken in conjunction with the accompanying drawings.

BRIEF DESCRIPTION OF THE DRAWINGS

FIG. 26 is a flow diagram illustrating the process for setting thresholds and gains.

DESCRIPTION OF THE PREFERRED EMBODIMENTS

Overview

Figure 1:
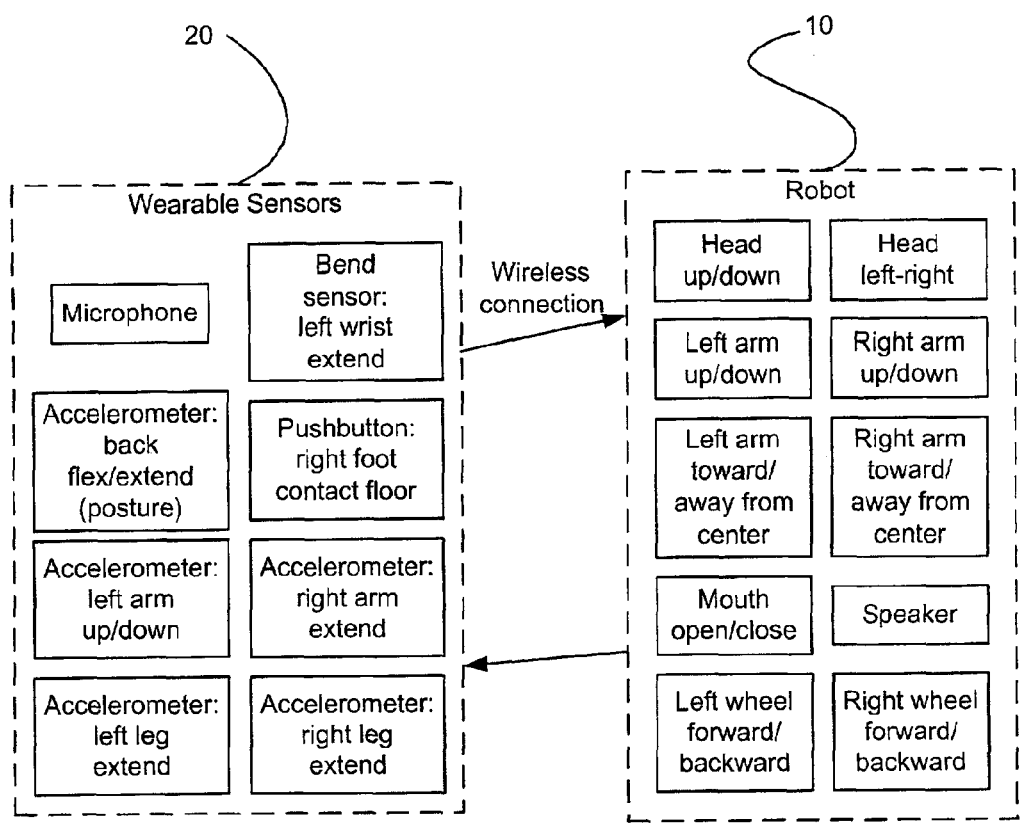
FIG. 1 is a block diagram of the interface and the associated robotic components.

FIG. 1 is a block diagram illustrating the elements of an interactive robotic apparatus. In its basic form, the apparatus includes a robot 10 and an interface 20. The robot 10 has a plurality of parts, which in a preferred embodiment may be representative of a human figure. The interface 20 includes a sensor and preferably a plurality of sensors. Each sensor may be placed in different locals and function to transmit a movement signal from the interface 20 to the robot. In one embodiment, the interface is synonymous with a set of wearable sensors. Different sensors may be placed along different locations of a user's body. For example, the user may wear an arm sensor and a leg sensor, which may be mapped to be in communication with an arm assembly and a leg assembly of the robot 10, respectively. Accordingly, each sensor that is a part of the interface unit 20 is preferably mapped to be in communication with a corresponding assembly of the robot 10.

Each sub-assembly of the robot 10 corresponding to a moveable body part includes an actuator in communication with a corresponding sensor of the interface 20. The robot includes a controller for receiving a signal from the interface unit 20 and translating the received signal to an appropriate actuator. Each set of actuators of the robot 10 controls movement of a corresponding actuator associated with an assembly of the robot. For example, an arm assembly includes a plurality of actuators that control movement of the arm of the robot in response to a signal received from an arm sensor of the interface 20. The user may wear a sensor of the interface 20 on a specific body part to control movement of a corresponding body part of the robot 10. The sensor of the interface transmits a signal to the controller which receives the signal and controls actuation of the corresponding body part of the robot 10. Accordingly, the robot provides feedback to the user in the form of moving the corresponding body part of the robot 10 in response to the received signal.

Technical Details

The Robot Apparatus

Figure 2:
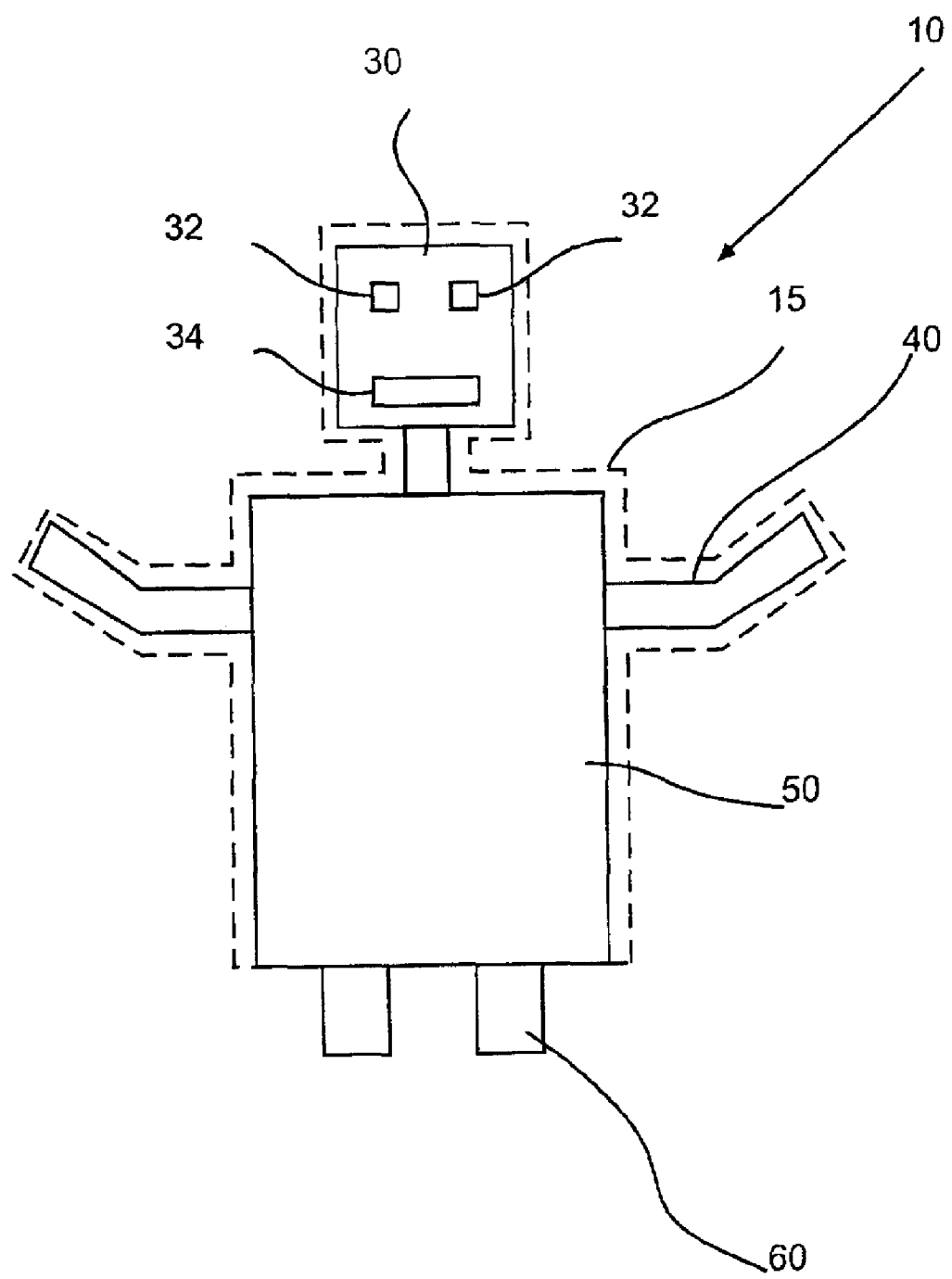
FIG. 2 is a graphical illustration of the robotic assembly.

The robot 10 may come in a variety of forms. One example of the robot 10 is shown in FIG. 2. The robot 10 includes a body 50 and a head 30 having facial components, including eyes 32 and a mouth 34. In addition to the facial components, the robot includes arms 40 and a leg chassis 60 to enable physical movement of the robot 10. Additional physical components may be incorporated into the robot 10 to enable additional movements and should not be considered limiting characteristics of the robot 10. Accordingly, the components illustrated in FIG. 2 are merely illustrative of examples of movements that are provided in the robot.

As shown in FIG. 2, the robot 10 may include a body assembly 50, an arm assembly 40, a leg chassis 60, and a head assembly 30. The arm assembly 40 is designed to enable vertical and lateral movement of the arm of the robot 10. The leg chassis includes a drive train assembly to enable forward and backward movement of the robot 10 along a planar surface, as well as rotational movement of the robot in a clockwise or counter-clockwise direction. The head assembly 30 enables pitch rotational movement of the head, as well as yaw rotational movement of the head assembly in a clockwise or counter-clockwise direction. A protective shell 15 surrounds the exterior components of the assembly and may include ornamental design components to enable the robot to exhibit different looks. Accordingly, the assemblies illustrated in FIG. 2 are illustrative of the physical parts of the robot that are responsive to sensors in communication with each of the illustrated assemblies.

Figure 3:
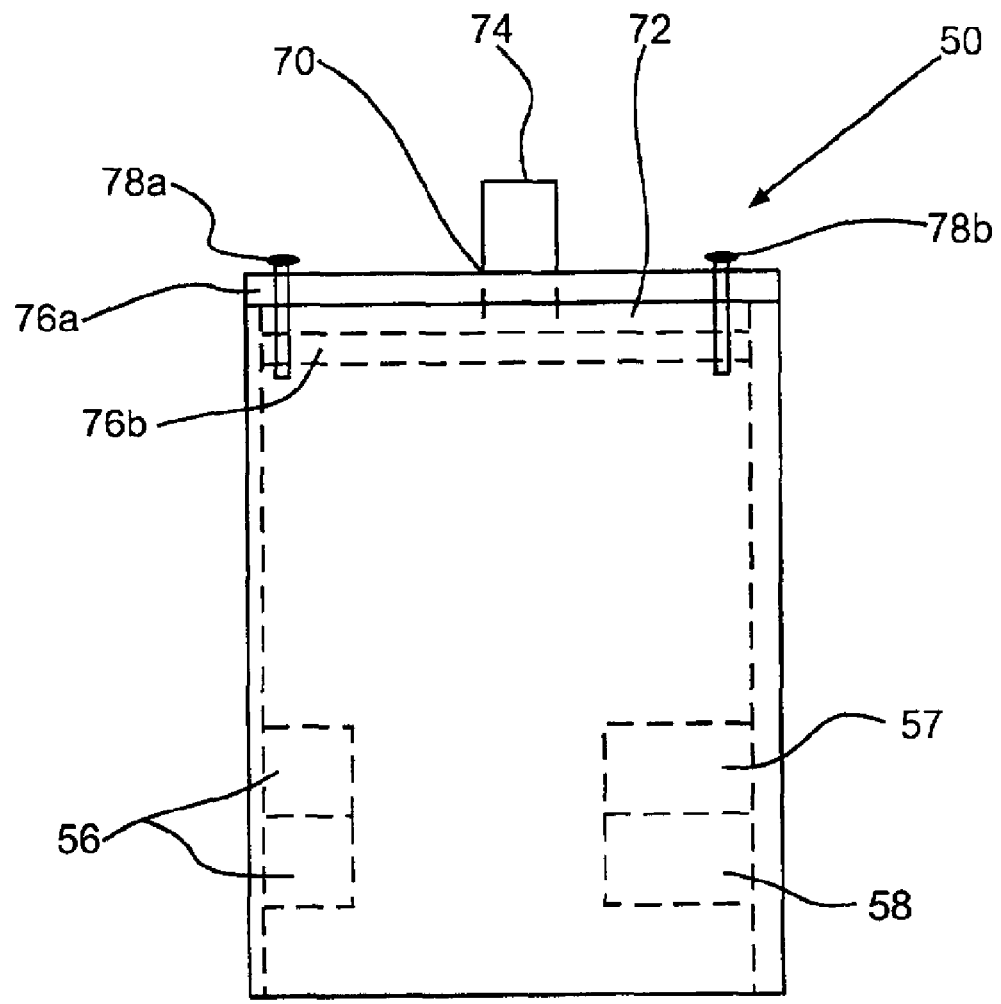
FIG. 3 is graphical illustration of the neck assembly of the robot.

The arm assembly 40, leg chassis 60 and head assembly 30 are each connected to different parts of the body 50 of the robot 10. FIG. 3 is a diagram illustrating the body of the robot 50 and the connection of the above identified assemblies 30, 40, 50 and 60 to different parts of the body. Between the body 50 and the head assembly 30 is a neck assembly 70 for attaching the head assembly 30 to the body 50. In a preferred embodiment, the neck assembly 70 may be in the form of a roll joint to facilitate rotation of the head assembly 30. There are different structures of roll joints that may be employed in the neck assembly 70. One example of a roll joint is shown in FIG. 3. The roll joint illustrated here includes a disc 72 soldered onto a rod 74 where the disc 72 is captured between two plates 76a and 76b. The disc 72 rotates freely between the two plates 76a and 76b. The roll joint is secured to a top area of the body 50 of the robot 10 with rivets 78a and 78b. The roll joint described herein is merely illustrative and may be modified to provide similar or additional movement capabilities of the head assembly 30 relative to the body 50 of the robot 10. In addition to the roll joint, FIG. 3 illustrates other components housed within the body 50, including a power supply 56, a transceiver 57 and a controller 58. The transceiver 57 and controller 58 receive power from the power supply 56. In addition, the transceiver 57 is adapted to receive signals emanating from a remote sensor or a remote console. The signals received by the controller 58 control operation of the assigned motors which control movement of specific assemblies within the robot 10. Accordingly, the structure of the roll joint enables the head assembly 30 to move in pitch and yaw directions upon actuation.

Figure 4:
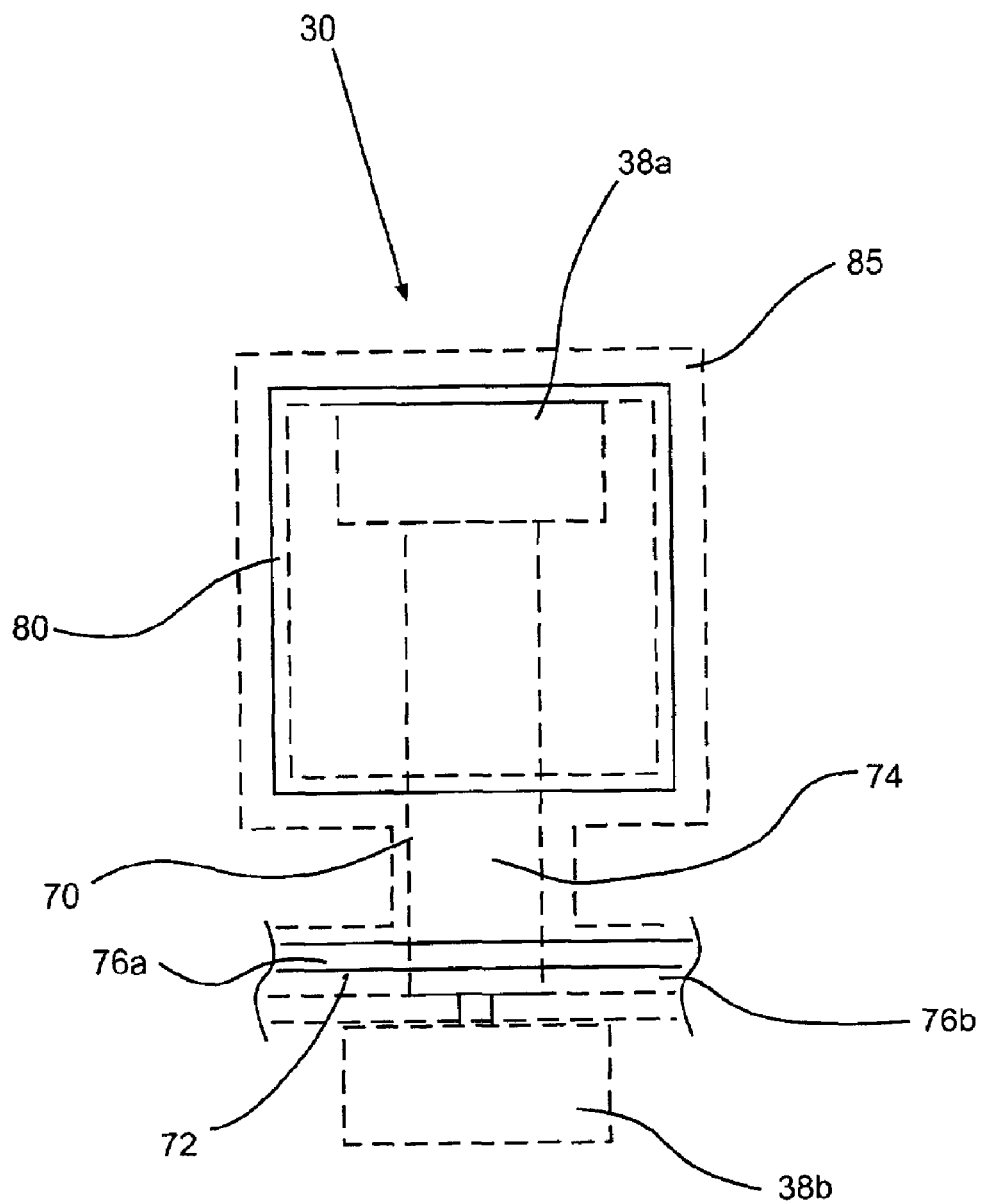
FIG. 4 is graphical illustration of the head assembly of the robot.

FIG. 4 is an illustration of the head 30 and neck assembly 70 of the robot 10. In this illustration, the head assembly 30 includes a first motor 38a and the neck assembly 70 includes a second motor 38b. The first motor 38a is connected to the roll joint of the neck assembly 70 and controls pitch movement of the head assembly, i.e. enables the head assembly 30 of the robot 10 to tilt in a forward or backward direction. More specifically, tilting of the head is controlled by the motor 38a mounted on rod 74 of the roll joint of the neck assembly 70. A box 80 encloses the first motor 38a and serves as a layer of protection for the first motor 38a from external elements. In addition, a head covering 85 is provided that encloses the first motor 38a, rod 74, and plates 76a, 76b of the roll joint. The first motor 38a controls tilt movement of the head assembly 30 by regulating relative movement between the rod 74 and the box 80 along a vertical axis. A second motor 38b is provided to control rotational movement of the head assembly 30 along a horizontal axis. Rotational movement is limited by the rod 74 and disc 72 of the roll joint of the neck assembly 70.

Figure 5:
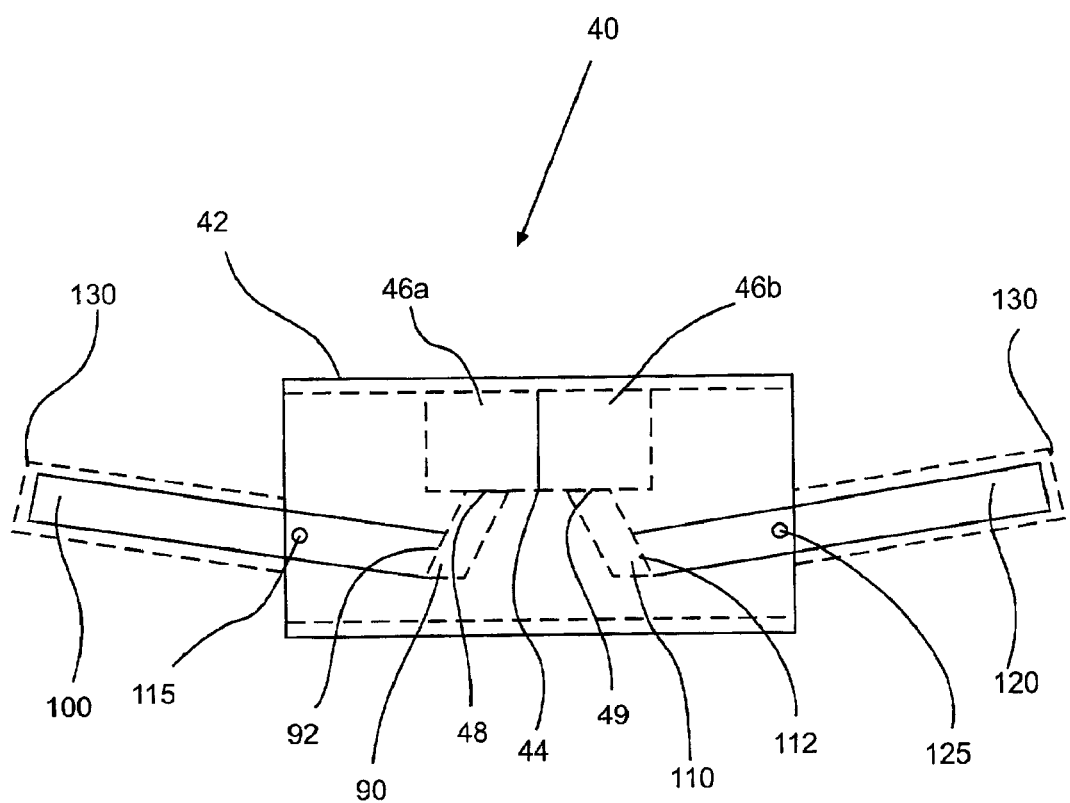
FIG. 5 is a graphical illustration of the arm assembly of the robot.

In addition to the body assembly 50 and head assembly 30 illustrated in FIGS. 3 and 4, respectively, the robot also includes an arm assembly. FIG. 5 is an illustration of a two arm assembly 40 of the robot 10. Since the illustrated robot imitates the body of a human form, the robot arm assembly includes two arms. However, the robot may be modified to include multiple arms in excess of the two illustrated or it may be limited to a single arm.

The arm assembly is enclosed by a cylindrical housing 42. The housing encloses an assembly 44, which includes a first motor 46a and a second motor 46b. Both the first motor 46a and the second motor 46b are secured to an interior surface of the cylindrical housing 42. In addition, the first motor 46a has a proximal end 48 with a first push rod 90 secured thereto, with the proximal end 92 of the first push rod 90 secured to a first lever arm 100. Similarly, a proximal end 49 of a second push rod 110 is secured to the second motor 46b, with the proximal end 112 of the second push rod 110 secured to a second lever arm 120. Both the first lever arm 100 and the second lever arm 120 include a pin 115 and 125, respectively, to limit the axis of rotation of each of the lever arms. Each pivot pin 115, 125 has a thrust bushing to limit off-axis rotation of each lever arm 100, 120, respectively. The arm assembly 40 is attached to the body 50 of the robot 10. Upon actuation, the rotary motion of the motor is converted to linear motion. In addition, each arm lever 100, 120 is received by a shell 130 designed to accommodate the physical attributes of the arms 100, 120 and to enable movement within the structural limitation of the design features of the arm assembly.

Figure 6:
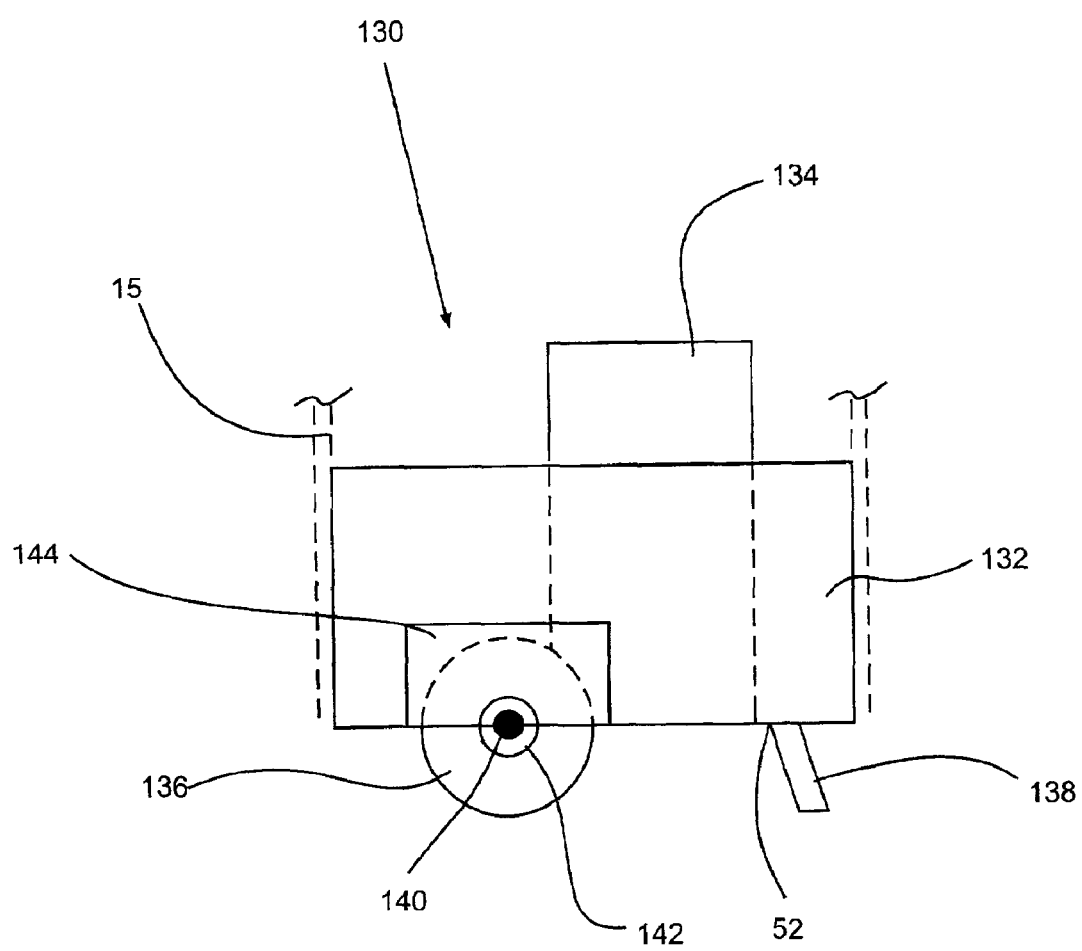
FIG. 6 is a graphical illustration of the drive train assembly of the robot.

In addition to the head assembly 30, neck assembly 70 and arm assembly 40, the robot 10 also includes a leg chassis 60 with a drive train assembly 130 to provide multi-directional movement of the robot 10. FIG. 6 is an illustration of one embodiment of the drive train assembly 130. The drive train assembly 130 is enclosed by a housing 132 secured to a bottom end 52 of the body assembly 50 of the robot 10. In addition, the housing 132 encloses a motor 134, a wheel 136, and a slider 138. The motor 134 is attached to an interior surface of the chassis 60. The motor 134 is secured to an axle 140 of the wheel 136 through a direct mechanical connection. The axle 140 is supported by two bearings 142 mounted on the chassis 60. Adjacent to the wheel 136 is a fender 144 to protect the wheel 136 from external elements. The slider 138 is preferably spring loaded and is secured to an underside of the chassis 60 and functions as a low friction point of contact on the planar surface on which the robot 10 is resting. The slider essentially prevents the robot 10 from tipping over during movement. Although only a single motor-wheel assembly is illustrated, the drive train assembly 130 may be designed with a plurality of motors and associated wheels. Accordingly, the drive train assembly 130 functions to enable the robot to move in a plurality of directions along a planar surface.

Figure 7:
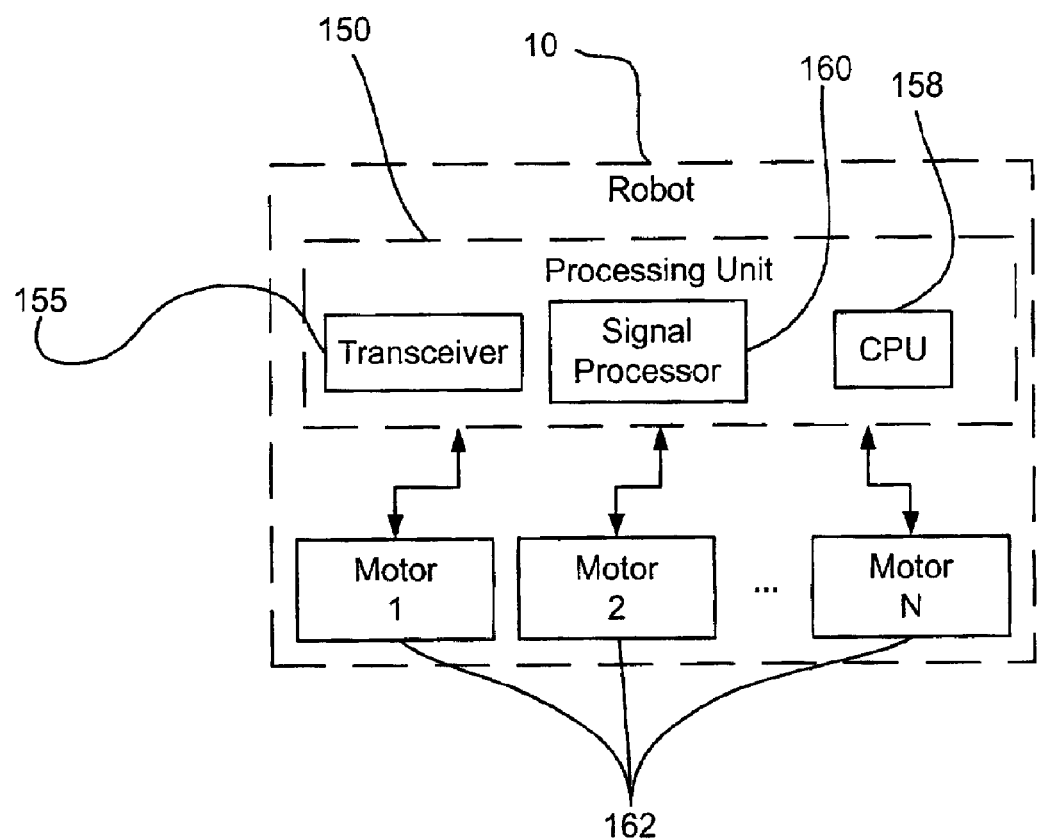
FIG. 7 is a block diagram of the robot with a central processing unit.

FIG. 7 is an illustration of the robot with a processing unit 150 for transmitting signals to remote sensors, as well as receiving signals from remote sensors. The processing unit 150 includes a transceiver 155 to send and receive signals, a signal processor 160 to process received signals, and a central processing unit (CPU) 158 for allocating the signals to a motor 162. The CPU 158 sends the processed signal from the processing unit 150 to an appropriate motor of an assembly of the robot 10. Each motor of the robot 10 is connected to the processing unit 150, either directly or indirectly, for receiving and transmitting movement signals to and from the motor of an assembly. In an alternative embodiment, the robot 10 may not include a processing unit 150. Rather, each motor of the robot 10 may include a transceiver to directly send and receive signals transmitted from a sensor. Accordingly, each motor or the processing unit 150 of the robot functions to control transmission and receipt of signals from a remote location and to actuate motors of appropriate assemblies.

Sensors

Figure 8:
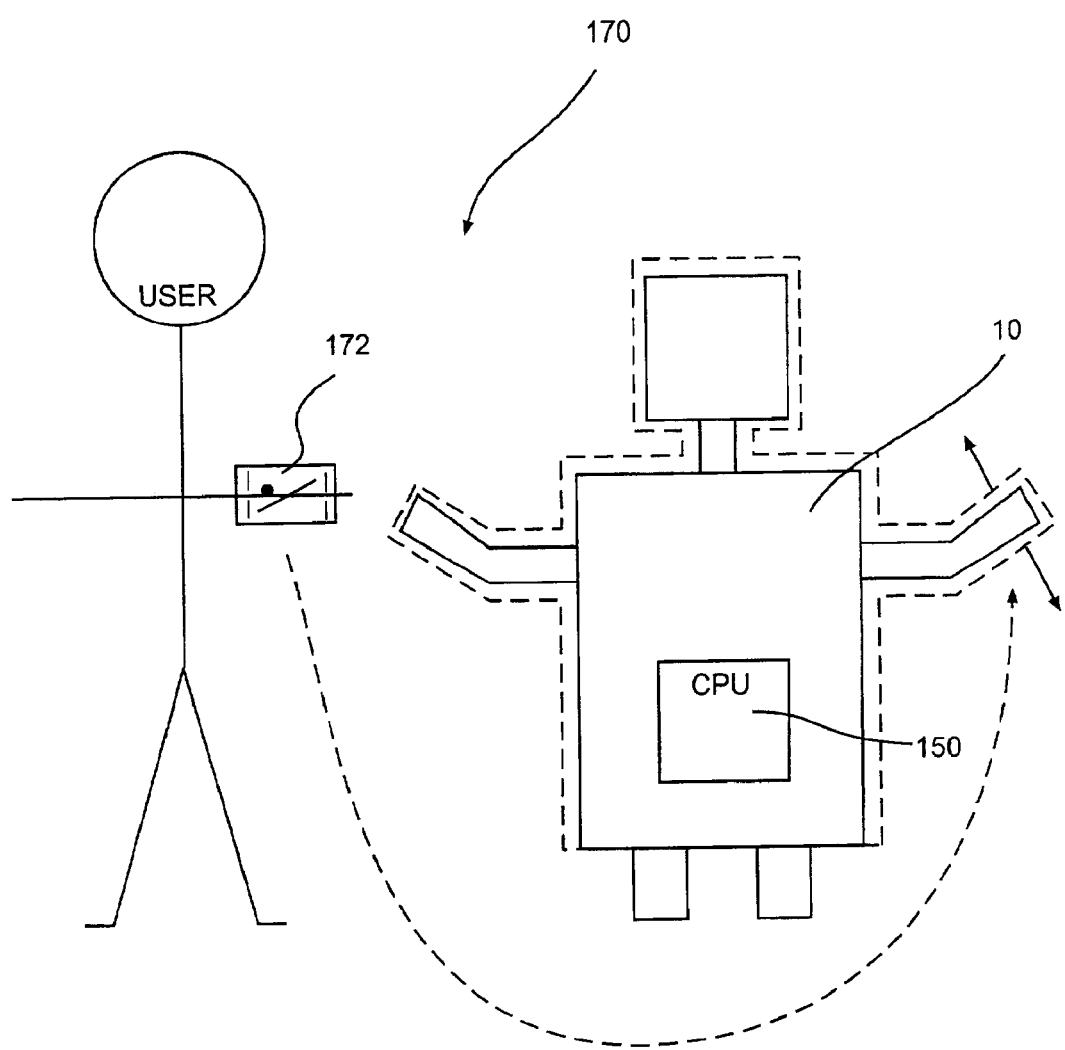
FIG. 8 is an illustration of a single wireless sensor in communication with a remote actuator.

In association with the robot 10 of FIGS. 2–7, a sensor or a network of sensors are provided to communicate with each of the motors of the robot 10 either independently or through the processing unit 150 of the robot 10. FIG. 8 is an illustration 170 of a single sensor 172 attached to a user remote from the robot 10. The sensor 172 may also include a power supply (not shown), a transceiver (not shown), and a signal processor (not shown). The sensor 172 is worn by the user on a specific locale of the body and may transmit body movement to the robot 10 through a wireless signal. Similarly, the transmitted signal is received by the processing unit 150 of the robot 10 where it is processed to provide feedback to the user. Feedback may be displayed in various forms, including direct feedback in the form of movement of a corresponding body part on the robot 10 to that of the sensor 172. Accordingly, this embodiment is an illustration of wireless communication from a single sensor to a motor of a remote robot 10.

Figure 9:
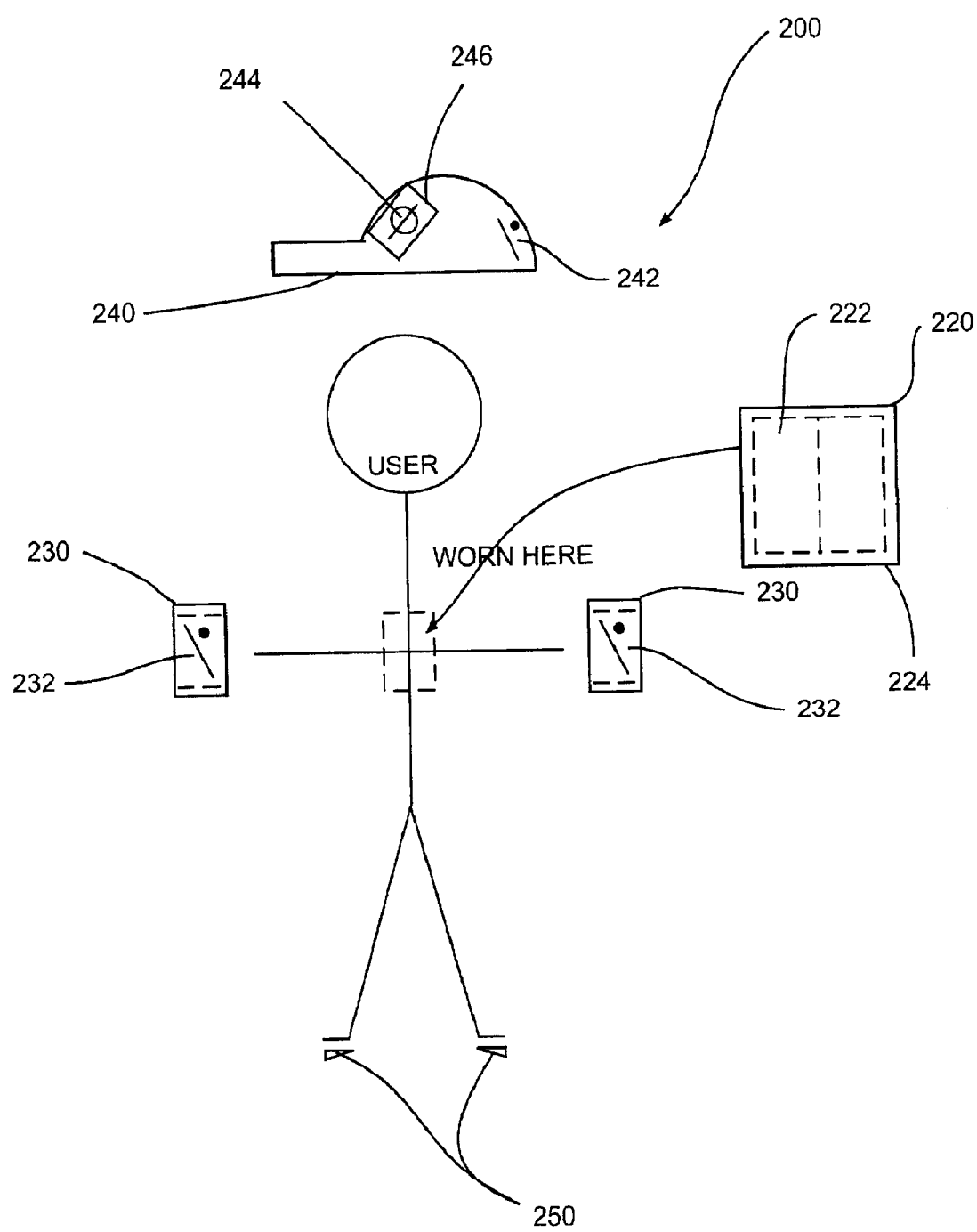
FIG. 9 is an illustration of a network of sensors in communication with a central unit.

FIG. 9 is an illustration 200 of a network of sensors that are in communication with a central unit 220. In this figure, the network of sensors is shown in association with the assemblies of the robot 10 illustrated in FIGS. 2–7. The central unit 220 houses a power supply 222 and a transceiver 224. The central unit 220 may be housed in a structure that is wearable by a user. For example, the central unit may be enclosed in a backpack, a fannypack, or a variety of enclosures that may be worn by a user. A wrist sensor 230 is shown secured to the wrist of the user in the form of a wrist band. The wrist sensor 230 includes a switch 232 secured to or sewn into the wrist band. The switch 232 of the wrist sensor is used to communicate movement of the wrist of the user to the arm assembly 40 of the robot 10. A head covering 240 is shown to be worn on the head of a user. The head covering 240 includes a switch 242 and a gyroscope 244. Both the switch 242 and the gyroscope 244 are sewn into or otherwise secured to the head covering 240. The gyroscope 244 is enclosed within a housing 246 within the head covering 240. When powered, the electronic components associated with the gyroscope 244 provide a variation in resistance during any linear acceleration on a specific plane. This variation in resistance is mapped directly to the electronic components in the transceiver 224 of the central unit 220. The switch 242 and the gyroscope 244 of the head covering are used to communicate movement of the head of the user to the head assembly 30 of the robot 10. Similarly, a switch 250 for sensing pressure is attached to the underside surface of the feet of the user. At such time as the user steps on the switch 250, the switch 250 absorbs the pressure of the user. Activation of the switch 250 controls translation and/or rotation of the drive train 130 of the robot 10. Each of the sensors 230, 240 and 250 and the gyroscope 244 may be tethered to the central unit 220 or may wirelessly communicate through radio frequencies. In a preferred embodiment, the switches 232, 242, and 250 are wired through 1.5 ohms of resistance and then to the potentiometer contact points in the transceiver 224. It should be understood that alternate sensors may be used as a matter of design choice to adapt the system to other forms of control or for use with many types of disabilities. For example, a microphone may be attached to the user to enable transmission of auditory signals from the user to the robot 10. Similarly, each of the sensors may be calibrated for different threshold values depending upon the desired range of movement of the user. Accordingly, the sensor network arrangement illustrated herein is merely an example of one form of a network assembly secured to a user and in wireless communication with a remote robot 10.

Figure 10:
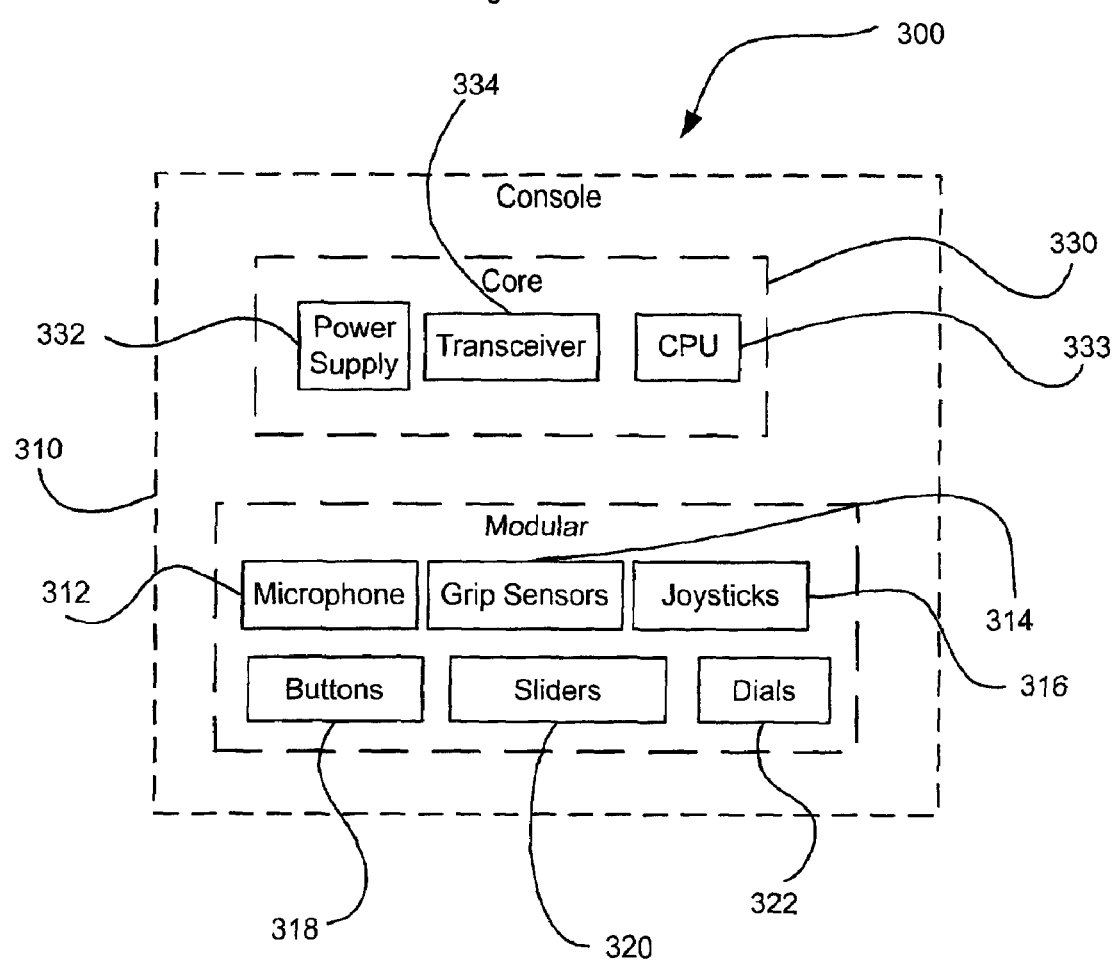
FIG. 10 is a block diagram of a console.

Another form of a network of sensors 300 is shown in FIG. 10. In this figure, the sensors are not worn by a user; rather the sensors are secured to a console 310 remote from the user. The console 30 includes sensors in the form of a microphone 312 for transmitting auditory signals, and sensors selected from the following group to control motors on the robot: a grip sensor 314, a joystick 316, a pushbutton 318, a slider 320, and dials 322. Other examples of sensors include, mechanical and electrical sensor apparatus selected from the following group: a force-reflecting joystick, a push-button, and a slider. The purpose of the console unit is to provide an alternative communication mode for communicating with the robot. The communication mode selected structure will be dependent on the rehabilitative exercise desired. Each of the sensors may be mapped to one or more motors on the robot. Upon actuation of the sensor(s), the appropriate motor on the robot will receive a communication signal. In addition to the sensors, the console includes a control unit 330 similar to the control unit of the sensor network 200 shown in FIG. 9. The control unit 330 includes a power supply 332, a transceiver 334, and a central processing unit 333. The control unit 330 of the console 310 may also include memory to record and save actuations of the sensors. In addition, the console may include a video monitor to display various modes of operation of the sensor-actuator system. For example, if the user or another operator selects to record and save sensor data, the user and/or operator, may later select to play the recorded movement of the sensors by the user and to display such recordings on the associated monitor. The console 330 illustrated herein may be designed to employ a variety of sensors and control mechanisms. Each sensor shown in FIG. 10 is merely illustrative of an example of sensors for communicating with the associated assemblies of the robot shown in FIGS. 2–6. In addition, the console may be designed for remote sensor capabilities without the ability to save, record, and/or play the movements of the user with the sensors. Accordingly, the console of FIG. 10 is merely an illustration of one form of a console adapted to communicate with the robot.

Signal Communication

Figure 11:
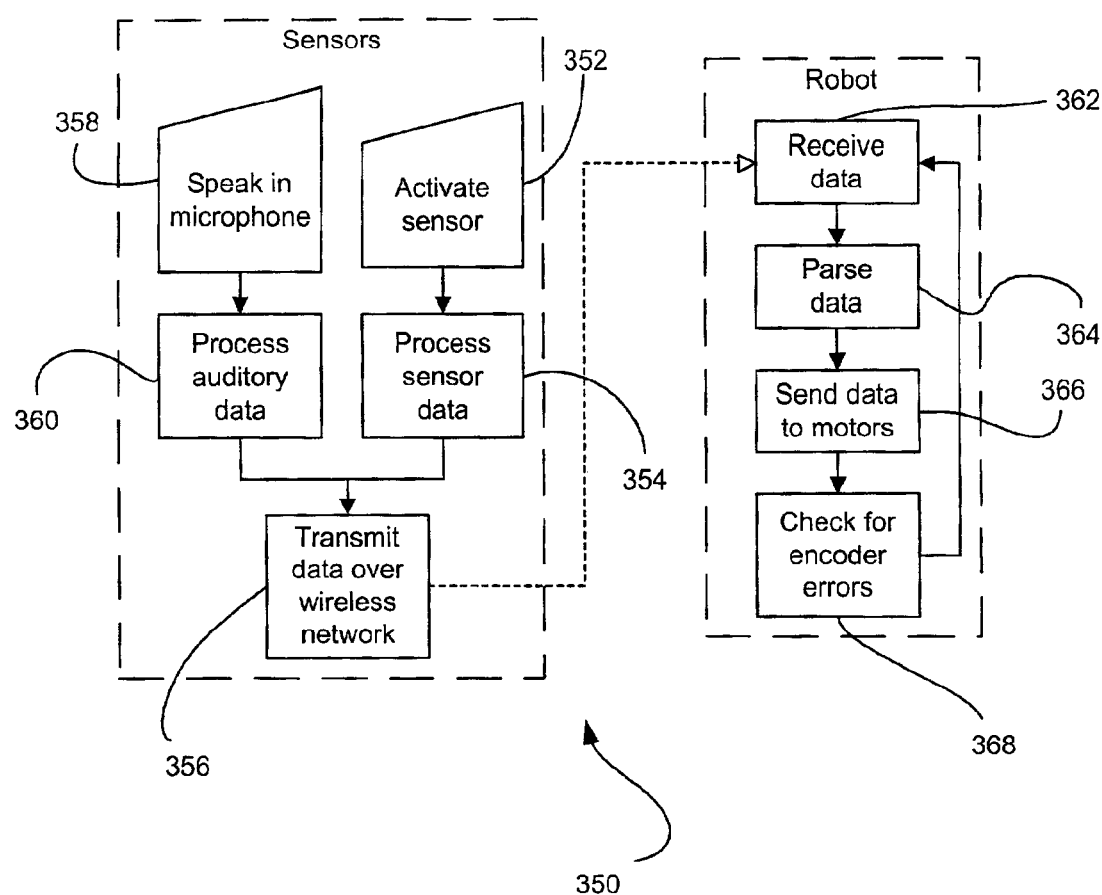
FIG. 11 is a flow diagram illustrating actuation of a sensor and processing of sensor data.

Both the control units 220 and 330 of the sensor network 200 and the console 310, respectively, are adapted to process and send signals received from the associated sensors to the mapped motors of the robot 10. Similarly, each of the control units 220 and 330 are adapted to receive signals from the processing unit of the robot 150 and to transmit the received signals to an appropriate assembly actuator. FIG. 11 is a flow chart 350 illustrating the flow user input data and how the data is processed and sent to an appropriate assembly on the robot 10 in a real-time control mode. This flow chart 350 illustrates the flow of a signal from a single sensor assembly or a sensor within a sensor network to the robot 10 in a real time control. In the case of a physical sensor worn by a user, the user changes the sensor input 352 by moving their body part that is secured to the sensor. The sensor data is then processed 354 and transmitted over a wireless network 356 by a transmitter or transceiver. Similarly, if the sensor is an auditory sensor, the user activates the sensor by speaking into the microphone 358. The auditory data is then processed 360 and transmitted over a wireless network 356 by a transmitter or receiver. In this example, the sensor is a single sensor assembly, and the transmitter and signal processor are incorporated into the individual sensor. Following transmission of the sensor signal data to the robot, the signal data is received 362 and subsequently parsed 364. The step of parsing the data 364 may include compressing or decompressing the signal data, mapping signal data, filtering the data, and/or determining if the signal data has attained a defined threshold. Following parsing of the data 364, the signal data is sent to a motor 366 in control of an assembly associated with the signal. The system then checks the signal to determine if there were any errors in the transmission from the sensor 368. Accordingly, in a single sensor real-time control mode, the signal is sent from the sensor to a motor in the robot to actuate an assembly in communication with the sensor.

Figure 12:
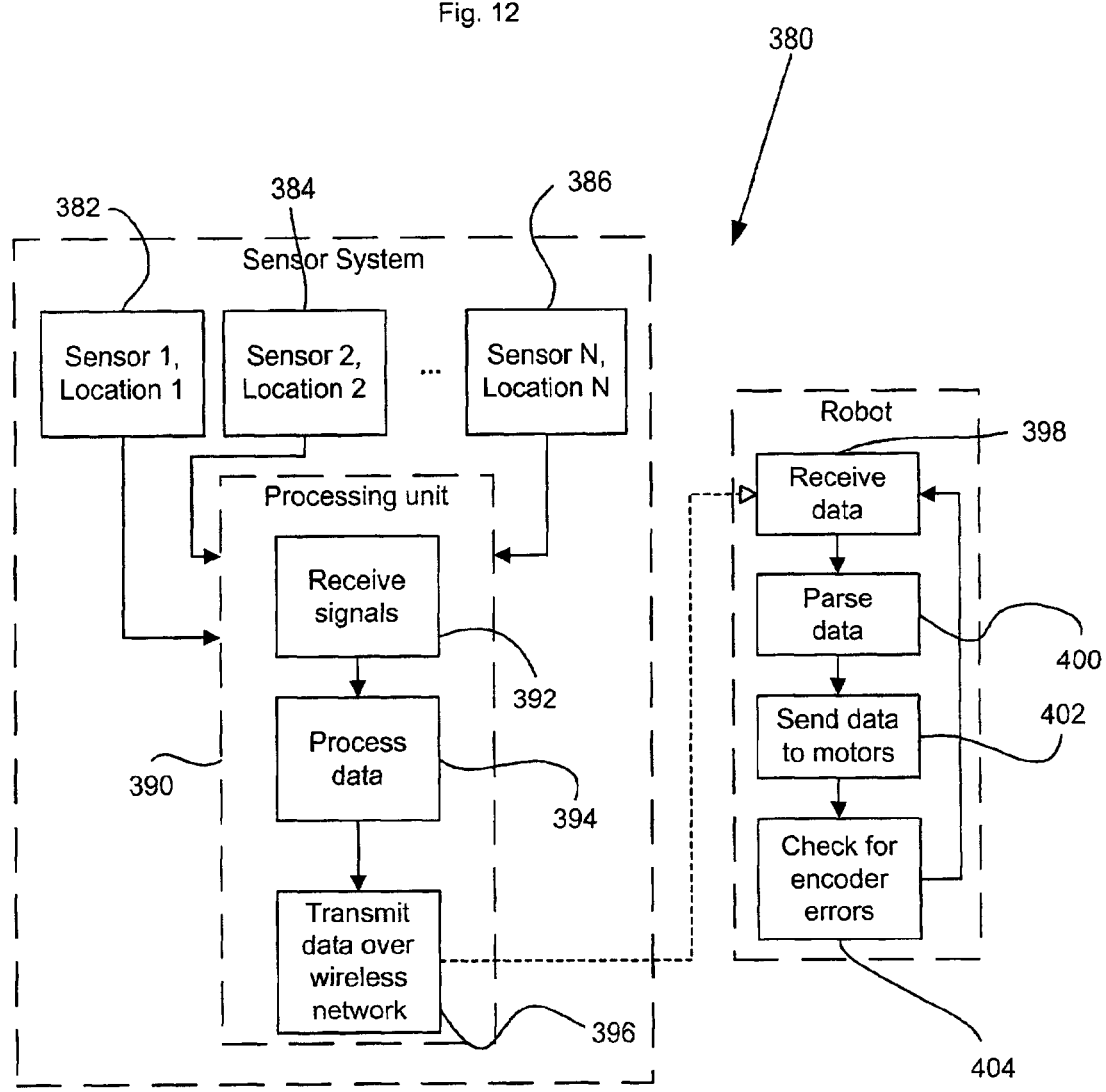
FIG. 12 is a flow diagram illustrating communication and processing of data from a wireless sensor.

FIG. 12 is an alternative embodiment to that shown in FIG. 11. FIG. 12 is a flow diagram 380 illustrating the monitoring of multiple sensors that are part of a wireless network, and further illustrates how the sensor data is processed and sent wirelessly to an appropriate assembly on the robot 10. As shown in FIG. 12, there are a plurality of sensors 382, 384 and 386, wherein each sensor is at a different location. The sensors 382, 384 and 386 are tethered together and connected to a single processing unit 390. The processing unit 390 receives the signals 392, processes the signal data 394, and transmits the signal data over a wireless network to a remote robot 396. Following transmission of the signal data to the robot, the signal data is received 398 and subsequently parsed 400. The step of parsing the data 400 may include decompressing the signal data, mapping signal data, filtering the data, and/or determining if the signal data has attained a defined threshold. Following the step of parsing the data 400, the signal is sent to a motor in control of an assembly associated with the signal in the case of a physical movement signal, or sent to a speaker in the case of auditory data 402. The system then checks the signal to determine if there were any errors in the transmission from the sensor 404. Accordingly, this embodiment is an illustration of a single network of remote sensors that communicate through a single processing unit, and following the processing of the sensor signal data the data is wirelessly transmitted to a remote robot in a real-time control mode.

Figure 13:
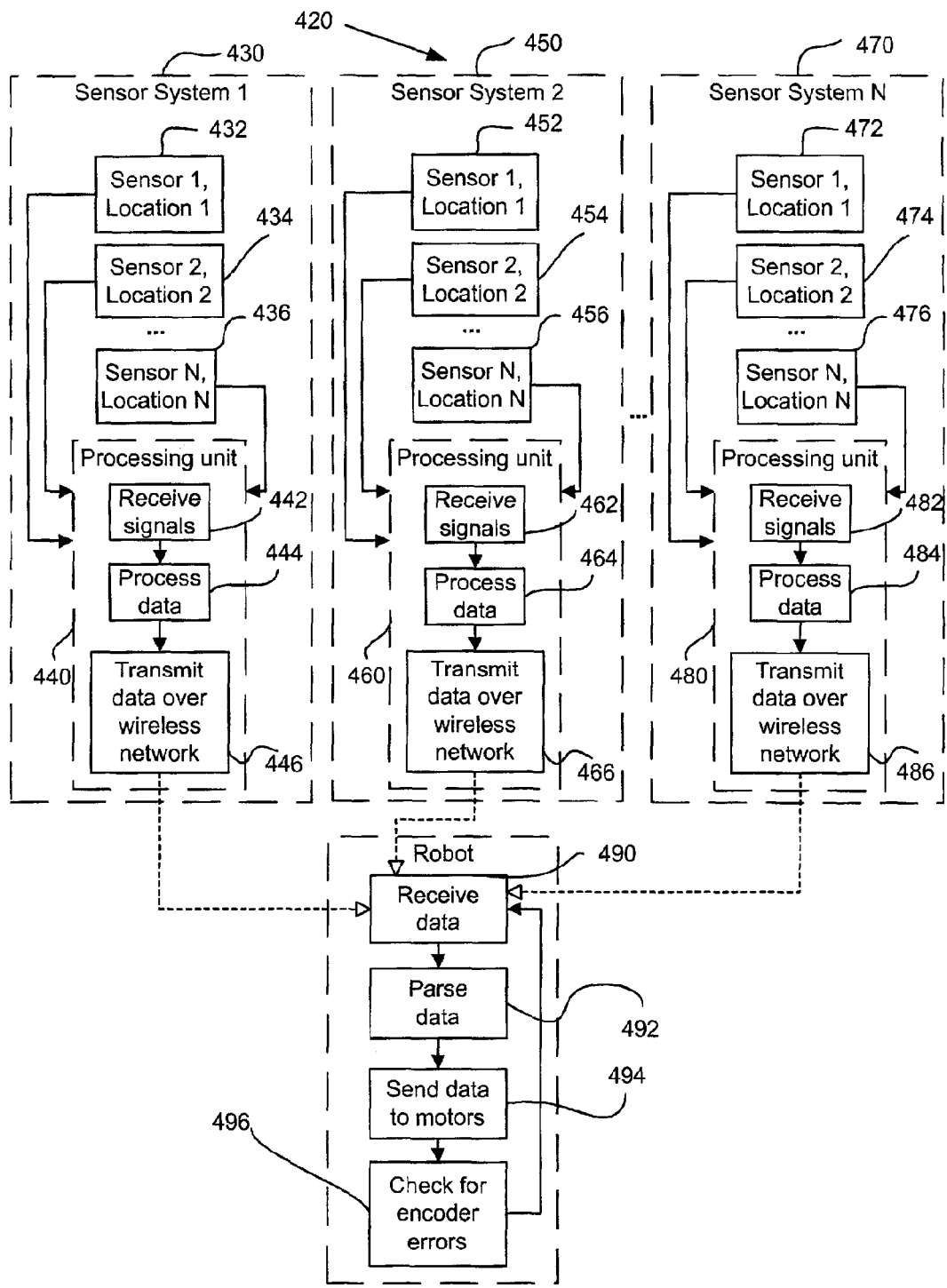
FIG. 13 is a flow diagram illustrating actuation of a wireless sensor that is part of a network of wireless sensors.

FIG. 13 is an alternative embodiment to that shown in FIG. 12. FIG. 13 is a flow diagram 420 illustrating the monitoring of multiple sensor sub-networks, and further illustrating how a network of wireless sub-networks communicate to transmit signals to a remote robot 10. The sensor system in FIG. 12 becomes sub-network 430 and the multiple sub-networks 430, 450, and 470 make up the wireless networks that communicate with the robot. As shown in FIG. 13, each sub-network has a plurality of sensors. A first sub-network of sensors 430 has a plurality of sensors 432, 434 and 436, wherein each sensor is at a different location. A second sub-network of sensors 450 has a plurality of sensors 452, 454 and 456, wherein each sensor is at a different location. A third sub-network of sensors 470 has a plurality of sensors 472, 474 and 476, wherein each sensor is at a different location. Each sub-network of sensors 430, 450 and 470 is part of a network of wireless sensors. Since the sub-networks are wireless, each sub-network 430, 450, and 470 has its own power supply and transceiver, in addition to the other components of the sensor. Each sub-network of sensors are tethered together and are connected to its own processing unit 440, 460 and 480, respectively. The appropriate processing unit receives the signal 442, 462 or 482, processes the signal data 444, 464 or 484, and transmits the signal data over a wireless network to a remote robot. Following transmission of the signal data to the robot, the signal data is received 490 and subsequently parsed 492. The step of parsing the data 492 may include compressing or decompressing the signal data, mapping signal data, filtering the data, and/or determining if the signal data has attained a defined threshold. Following the step of parsing the data 492, the signal is sent to a motor in control of an assembly associated with the signal 494 in the case of a physical movement signal, or sent to a speaker in the case of auditory data. The system then checks the signal to determine if there were any errors in the transmission from the sensor 496. Accordingly, this embodiment is an illustration of a plurality of networks of remote sensors wherein each network communicates signal data through their own processing unit and, following the processing of the sensor signal data, the data is wirelessly transmitted to a remote robot in a real-time control mode.

Figure 14:
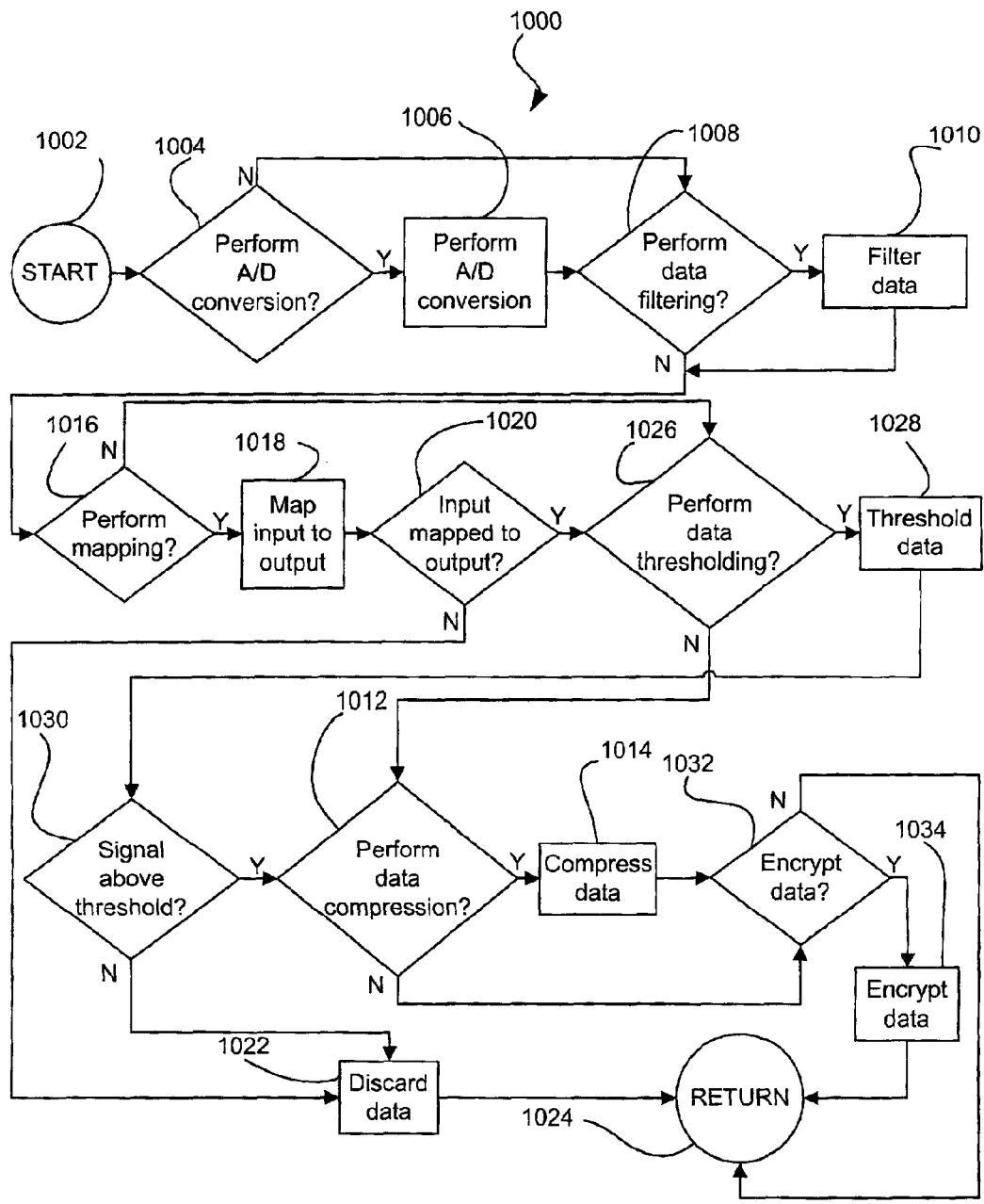
FIG. 14 is a flow chart illustrating the process of processing sensor data.

As shown in FIGS. 11, 12 and 13, the sensor is in communication with a remote robot. Sensor data is continually monitored and processed. FIG. 14 is a flow chart 1000 illustrating the process of processing sensor data for transmission to a remote actuator. When the sensor data is read 1002, the signal processor must determine if the signal requires an analog to digital conversion process 1004. If the switch on the sensor is an analog switch, then the signal processor performs a conversion of the sensor data from an analog format to digital format 1006. However, if the switch is a digital switch, then the signal processor proceeds to step 1008 from step 1004 to determine if filtering of the signal data is necessary. If the answer to the query at 1008 is positive, the signal processor filters the signal data 1010. Following the filtering of the signal data at 1010 or if the answer to the query at 1008 is negative, the signal processor then determines if a mapping of the signal data to a corresponding actuator should be conducted 1016. If it is determined that the mapping step 1016 is necessary, the signal data from the sensor is mapped to the appropriate actuator for the output 1018. The system then queries if the input of the signal data is mapped to the output of the actuator 1020. If the answer to the query at step 1020 is negative, the signal data is discarded 1022 and the system returns to receive signal data from the sensor 1024. However, if at step 1016 it is determined that it is not necessary to map the sensor signals to the actuator, or if at step 1020 it is determined that the input of the sensor signal is mapped to the actuator, then the system determines if the signal data must be compared to a minimum threshold 1026. If the answer to the query that signal data must meet a minimum threshold level is positive, the threshold data is attained at 1028, and the signal processor determines if the signal data from the sensor has met or exceeded the defined threshold 1030. However, if the sensor signal data has not met or exceeded the defined threshold at step 1030 the signal data is discarded 1022 and the system returns to receive signal data from the sensor 1024. Alternatively, if at step 1026 it is determined that the sensor signal data does not have to reach a minimum threshold or if at step 1030 it is determined that the sensor signal data has met or exceeded the defined threshold, the signal processor must then determine if the signal data should be encrypted 1032. If the signal data should be compressed 1012. If the answer to the query at step 1012 is positive, the signal data is compressed 1014. Following the compression of the signal data at 1014 or if the answer to the query at 1012 is negative, the signal processor then determines if the signal data should be encrypted. If the signal data should be encrypted, the signal data is encrypted at step 1034. Thereafter, the signal data proceeds directly to transmission to the output of the actuator. Alternatively, if at step 1032 it is determined that the data does not have to be encrypted, the signal data proceeds for transmission to the output of the actuator. Accordingly, FIG. 14 outlines the steps involved in processing signal data prior to forwarding the signal for transmission to the signal processor of the robot.

Figure 15:
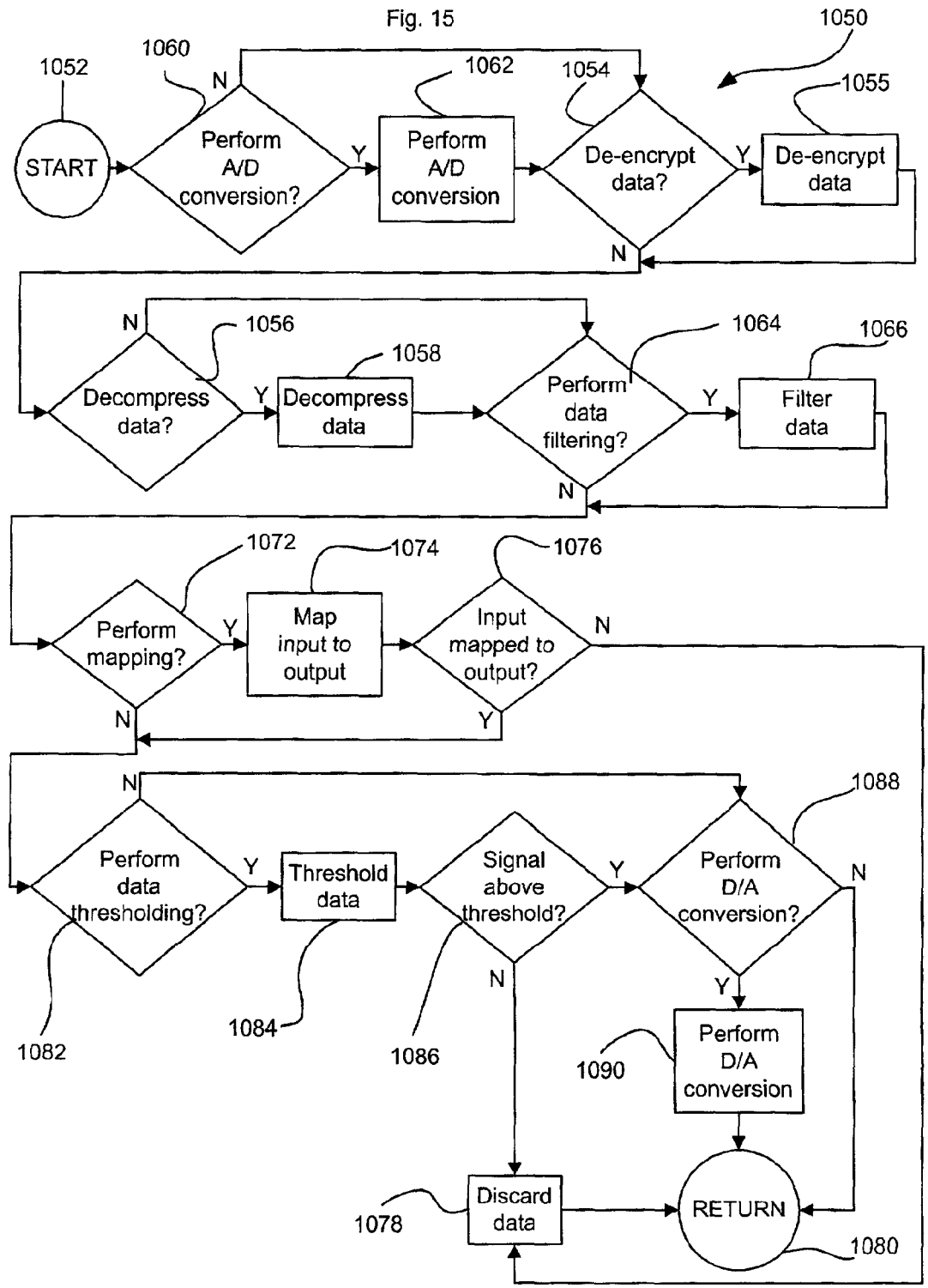
FIG. 15 is a flow chart illustrating the process of parsing sensor data.

Following the processing of the signal data from the sensor and transmission of the signal data from the sensor, sensor network, or console, the signal data is received by a signal processor of the robot. FIG. 15 is a flow chart 1050 illustrating the process of parsing the signal data upon receipt by the signal processor of the robot 1052. The signal processor must first determine if the signal data needs to proceed through an analog/digital conversion 1060. Generally this step is necessary if the signal data was transmitted in digital form and the processing unit 150 is adapted to receive data in an analog format. If the actuator requires analog data, the signal processor proceeds to step 1062 to convert the signal data from digital format to analog format. Following the data format conversion or if the signal data at step 1060 did not have to proceed through the conversion process of step 1062, the signal processor then determines if the signal data requires if the received signal data was encrypted 1054. If the signal data was encrypted, the signal data must be de-encrypted 1055. Following the step of de-encrypting the signal data 1055 or if the signal data was not encrypted, the system must then determine if the signal data was compressed 1056. If the signal data was compressed, the signal data must be decompressed 1058. Following the decompression of the signal data at 1058 or if it is determined that the signal data was not compressed, the signal processor proceeds to determine if the signal requires filtering 1064. If the answer to the query at step 1064 is positive, the system proceeds to step 1066 to filter the signal data. Following the filtering of the signal data at 1066 or if the signal data does not require filtering, the signal processor then determines if the signal data requires compression prior to forwarding the signal data to the actuator and associated motor 1068. If the processing unit 150 is adapted to receive compressed data, the signal processor compresses the signal data 1070 and proceeds to step 1072 to determine if the signal data needs to proceed through a mapping procedure for an appropriate actuator. Similarly, if at step 1068 it is determined that the signal data does not need to be compressed, the signal processor proceeds to step 1072 for the mapping determination. If the signal data requires additional mapping, the signal processor proceeds to map the signal data to an appropriate actuator 1074. However, if the received signal data does not map to an actuator 1076, the signal processor discards the signal data 1078 and the signal processor returns to receive and process subsequent signal data 1080. If at step 1072 the signal processor determines that additional mapping is not necessary or if at step 1076 the signal processor does properly map the signal data to an appropriate actuator, the signal processor proceeds to determined if the signal data needs to be compared to a defined threshold 1082. Based upon a pre-programmed threshold, the signal processor obtains the threshold 1084 data and proceeds to determine if the signal data has met or surpassed the threshold data 1086. If the signal data has not met or exceeded the threshold data at 1086, the signal data is discarded 1078 the signal processor returns to receive and process subsequent signal data 1080. However, if the signal data has met or exceeded the threshold data or if at step 1082 it is determined that the signal data does not have to meet a predefined threshold, the signal processor then determines if the processing unit requires the signal to proceed through an analog-digital conversion process 1088. If it is determined that the signal data is in a compatible format for receipt by the actuator, the signal data is forwarded to the proper actuator and the signal processor returns to receive additional signal data 1080. However, if the signal data is not in a compatible format for receipt by the actuator, the signal data is processed through an analog-digital conversion 1090 prior to forwarding to the proper actuator. Accordingly, FIG. 15 outlines the steps involved in parsing signal data upon receipt by a signal processor of the robot.

Figure 16:
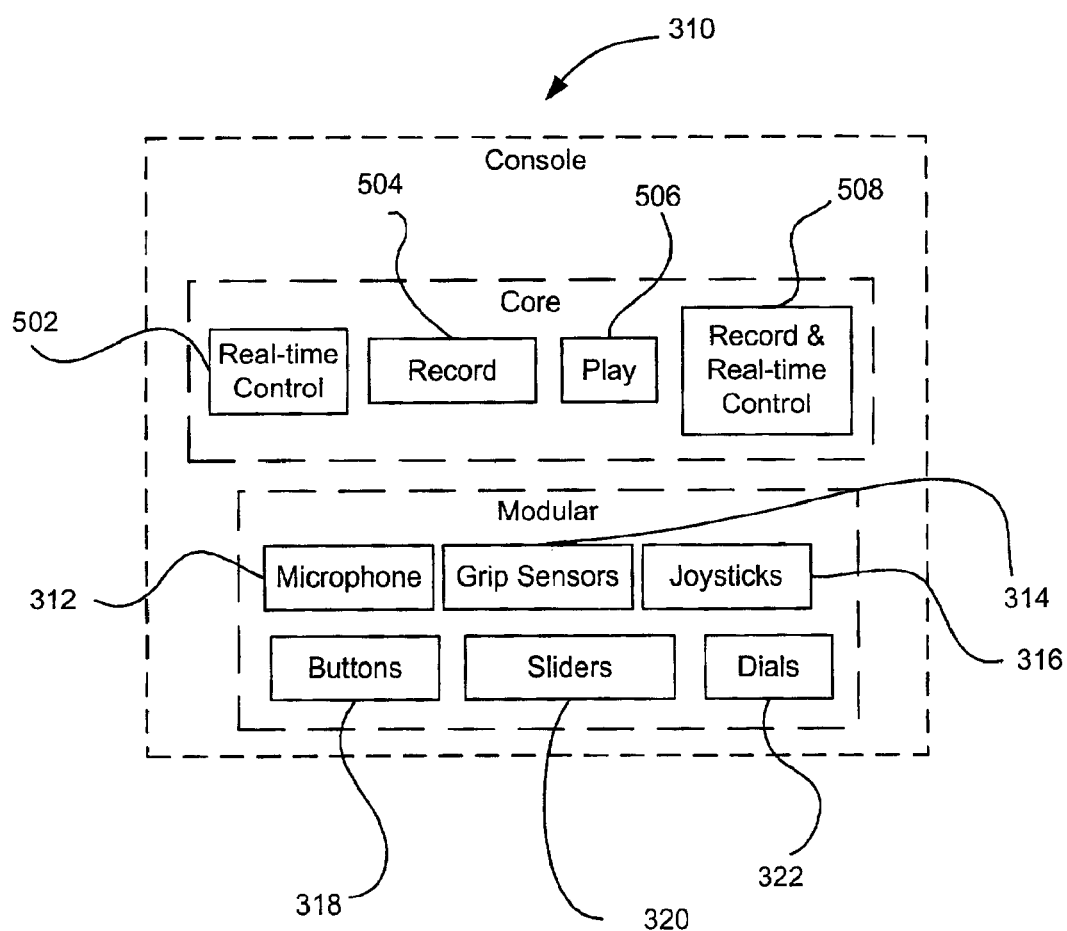
FIG. 16 is a block diagram of a console with mode selection capability.

As shown in FIGS. 11, 12 and 13, the system can function in association with a sensor or a network of sensors in wireless communication with an actuator. In addition, the system can function from sensors mounted on a console remote from the robot. The console 310 is adapted to operate in one of four modes: real-time 502, record 504, play 506, or record and real-time control 508. FIG. 16 is a block diagram 500 of a console with a mode selection capability. Prior to initiating interaction with the robot 10, the user should select the mode of operation. As shown in FIG. 16, the console may include an array of buttons 502, 504, 506 and 508, with each button having indicators adjacent to the button to indicate the mode of operation associated with the button. The console continues to be equipped with modular components 312, 314, 316, 318, 320 and 322. In addition, the console may be expanded to include a graphical user interface and central processing unit. In this embodiment, the user may select the mode of operation 510 of the robot through a modular interface. Accordingly, the console may be expanded to include a modular mode selector to enable the operator to select a mode of operation.

Figure 17:
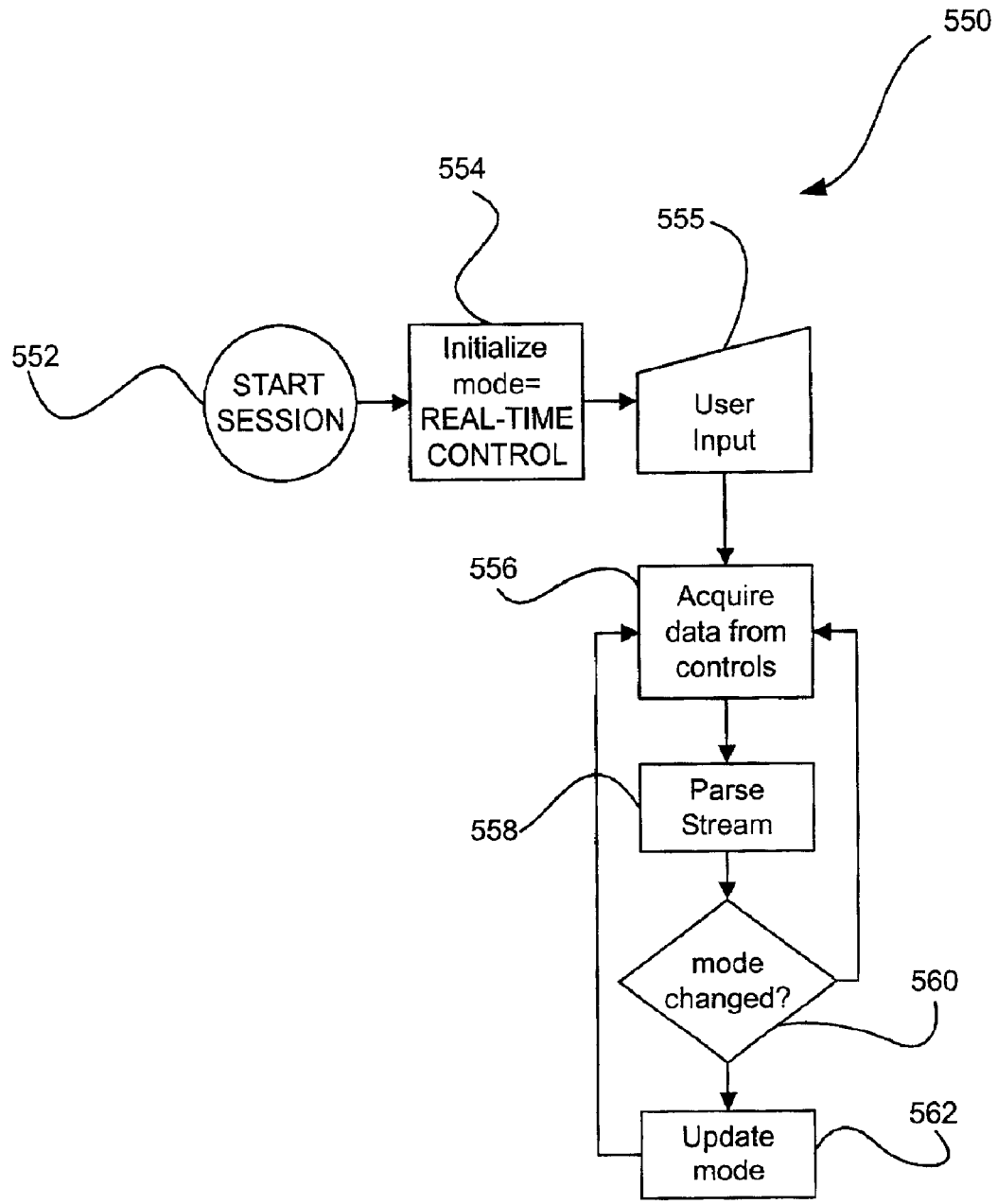
FIG. 17 is a flow chart illustrating the selection of a mode of operation.

FIG. 17 is a flow chart 550 illustrating the selection of a mode of operation through the console or a graphical user interface associated with the console. The default mode of operation is real-time control. At the start of the session 552, the mode is initialized to the default mode of real-time control 554. Thereafter, the mode may be changed by the user through mode selection 555. The mode selection 555 is acquired from the appropriate control of the console 556. The data of the mode selection is then parsed 558. It must then be determined if the user has selected to change the mode of operation 560. If the user has selected a mode other than the default mode of operation, or an alternatively assigned mode, then the mode of operation is updated 562 and acquired from the appropriate control of the console 556. Otherwise, the default mode or alternatively selected mode of operation remains in effect. Accordingly, the user and/or operator has the ability to select the mode of operation either at the beginning of a session or at a subsequent stage in operation of the robot 10.

Figure 19:
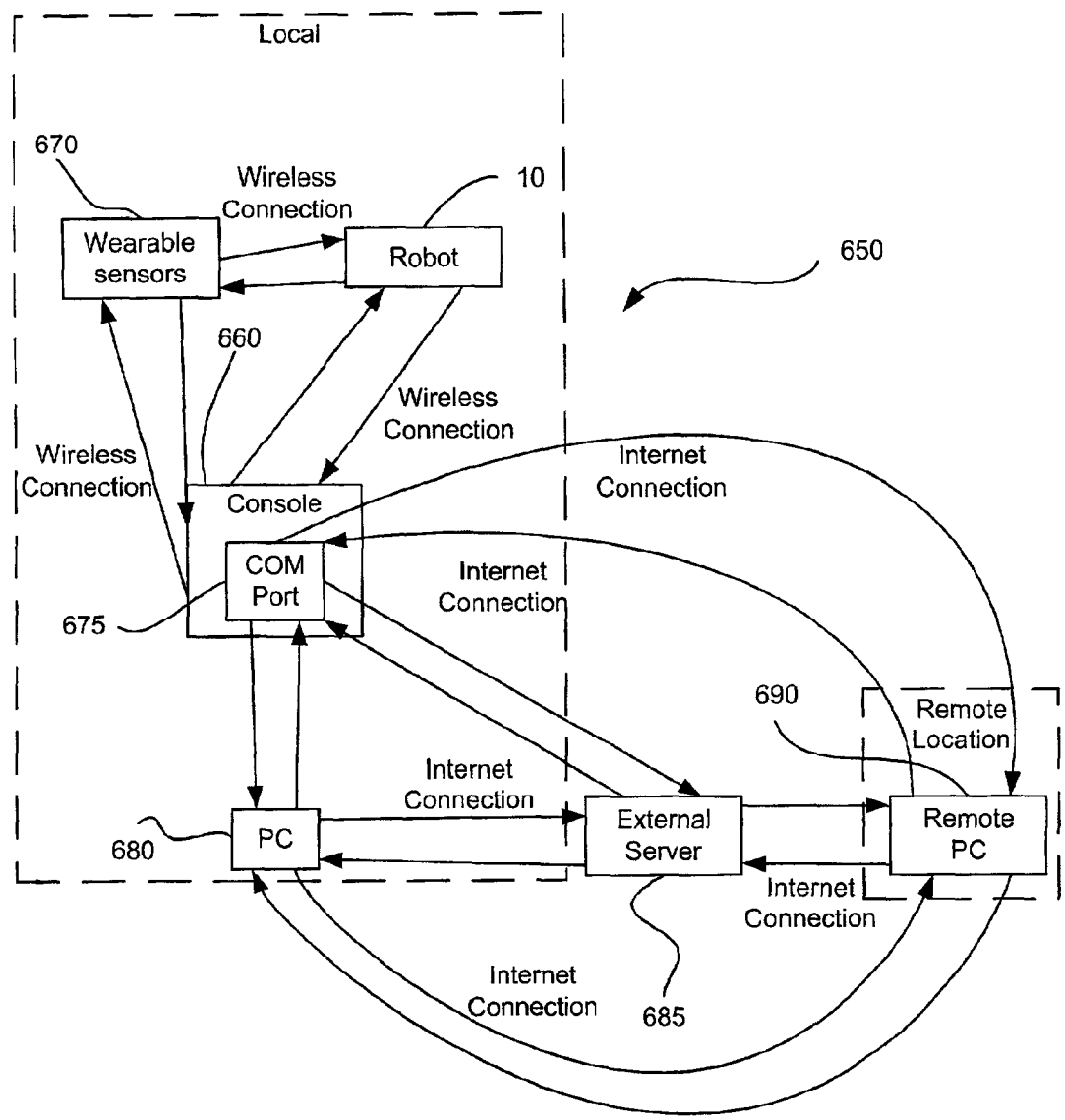
FIG. 19 block diagram illustrating the communication capabilities of the system.

The console unit functions as a unit for communicating data from sensors secured to the console to the robotic apparatus. Similarly, the console may contain a central processing unit for storing recorded files of data from the sensors and for transmitting saved files of data to the robotic apparatus 10. As shown in FIG. 19, the communication system 650 may include a console 660 is in wireless communication with the robotic apparatus 10 and may be similarly in wireless communication with a wireless (wearable) sensor or a network of wireless sensors 670. The functions of the console 660 in communication with the robotic apparatus 10 include a plurality of functions including mode selection and signal communication. The functions of the network of sensors 670 in communication with the robotic apparatus are outlined above and shown in FIGS. 11, 12 and 13. In addition, the system 650 may be configured with the network of wireless sensors 670 to be in communication with both the robotic apparatus 10 and the console 660. With the addition of memory to the console 660, the console can be expanded to receive and store sensor data from a wireless sensor 670 in addition to the sensors connected to the console unit 660. Accordingly, the robotic apparatus may be expanded to include wireless communication with the robotic apparatus from a remote sensor secured to a console, as well as a remote sensor secured to an independent object or person.

In addition to the expansion of the system to communicate sensor data from a console and a remote sensor 670 or sensor network, the console may be expanded to include a central processing unit. The purpose of the central processing unit is to expand the storage and memory capabilities of the console. This enables the console 660 to store sensor data and to playback sensor data at a later time. In addition, the central processing unit of the console 660 may be expanded to include a communication port 675, for connection to a personal computer 680 and 690 or an external server 685. The communication port 675 enables transfer of data between the console and a computer 680 with expanded capabilities. The computer 680 may then communicate with an external computer 690 directly or via an external server 685 through an Ethernet or alternative communication platform. In addition, if the console 660 is expanded to include a central processing unit with a communication port 675, then the console may communicate directly with a remote personal computer 690 or network server 685 through an Ethernet connection or an alternative communication platform. By maintaining the connection from an external computer 685 to the console 660, a remote user of the system can interact with the system in many ways: monitor the session, remotely interact with the robot, download data from the session, and communicate with the local user. In addition to providing an indirect link to a remote PC 690, the communication connection between the external server 685 and the console 660 or the local PC 680 also allows the local user to download new games and stories from the external server 685. Accordingly, the expansion of the console unit for communication with an external computer expands the functionality of the system and provides support for communicating with the system through a telecommunication network.

Figure 18:
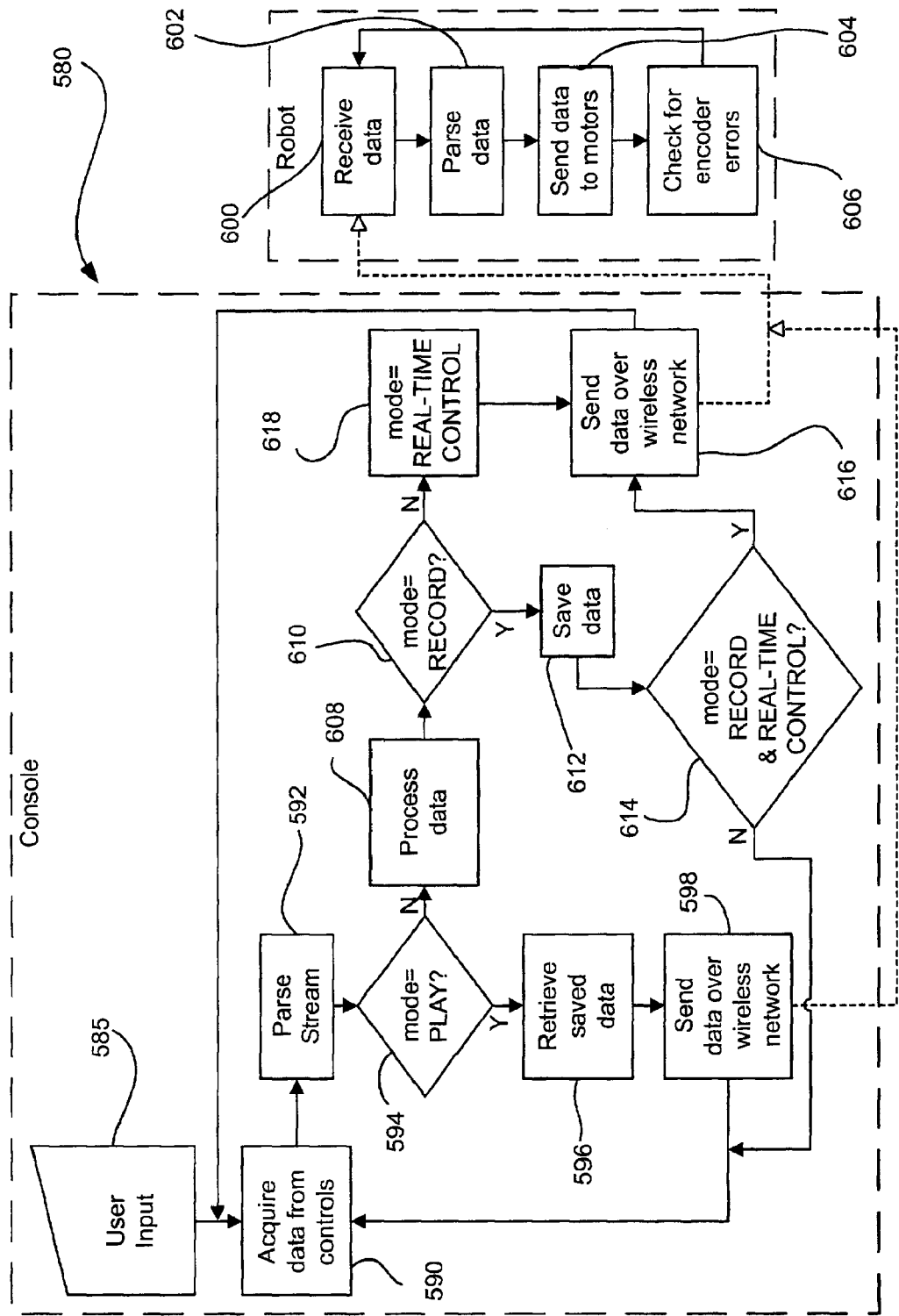
FIG. 18 is a flow diagram illustrating the flow of data from the console to the robot.

The default mode of operation of the console and associated robot 10 is real-time control. In a real-time control mode, a sensor on the console is activated to initiate control of the associated motor of the robot 10. The flow of data from the sensor to the appropriate assembly and motor on the robot is similar to the flow illustrated in FIG. 11. FIG. 18 is a flow diagram 580 illustrating the flow of data from the console to the actuator on the robot. The user provides input by moving or otherwise activating one of the controls on the console 585. If a microphone is provided as a sensor on the console, the input may be auditory in nature. The sensor data are then acquired from the controls of the console 590. Following the step of acquiring the data, the stream of data is parsed 592. Parsing is performed to separate and identify signals acquired from multiple controls which are embedded together in the input data stream. Following the parsing step 592, the system determines the mode of operation. If the mode of operation is to play previously recorded data 594, then the data must be retrieved from the saved location, presumably from the console 596, and sent over the wireless network to the robotic apparatus 598. Following transmission of the data file to the robot, the data stream is received 600 and signals in the data are subsequently parsed 602. The step of parsing the data may include mapping signal data, filtering the data, and/or determining if the signal data has attained a defined threshold. Following parsing of the data 602, the signal data are sent to a motor 604 in control of an assembly associated with the signal. The system then checks the signal to determine if there were any errors in the transmission from the console 606. Accordingly, in play mode, signal data are sent from the data file to a motor in the robot, either directly or through a central processing unit, to actuate an assembly in communication with the sensor.

If at step 594 in FIG. 18 it is determined that the mode of operation is not to play a previously recorded data file, the system processes the data 608. The step of processing the data may include: compressing the data, mapping the data, thresholding the data, filtering the data, and recognition of patterns within the data. Subsequently, if the mode of operation is set to record the data 610, the data are saved in a file 612. The mode of operation is either to simply record the data or to record and play the data in real-time. If the current mode is set to simply record 614, the system returns to step 590 to accept additional data from controls of the console. However, if the current mode is combined record and real-time control, the data are transmitted over a wireless network to the robot 616 contemporaneously with the data file being saved in the console. Similarly, if at step 610, the response to the query is negative, the system is in the default mode, real-time control 618, and sends the processed data over a wireless network to the robot 616. Following transmission of the data to the robot at step 616, the data are received 600 and the data are subsequently parsed 602. The step of parsing the data may include compressing or decompressing the signal data, mapping signal data, filtering the data, and/or determining if the signal data has attained a defined threshold. Following parsing of the data 604, the signal data are sent to a motor 604 in control of an assembly associated with the signal. The system then checks the signal to determine if there were any errors in the transmission from the console 606. Accordingly, whether in play, record-and-real-time control, or real-time control, processed signal data are sent from the console to a motor in the robot, either directly or through a central processing unit, to actuate an assembly in communication with the actuated sensor. In addition, if the current mode is to record data, data are saved, after being processed, on the console's central processing unit to be played at a later time.

Figure 20:
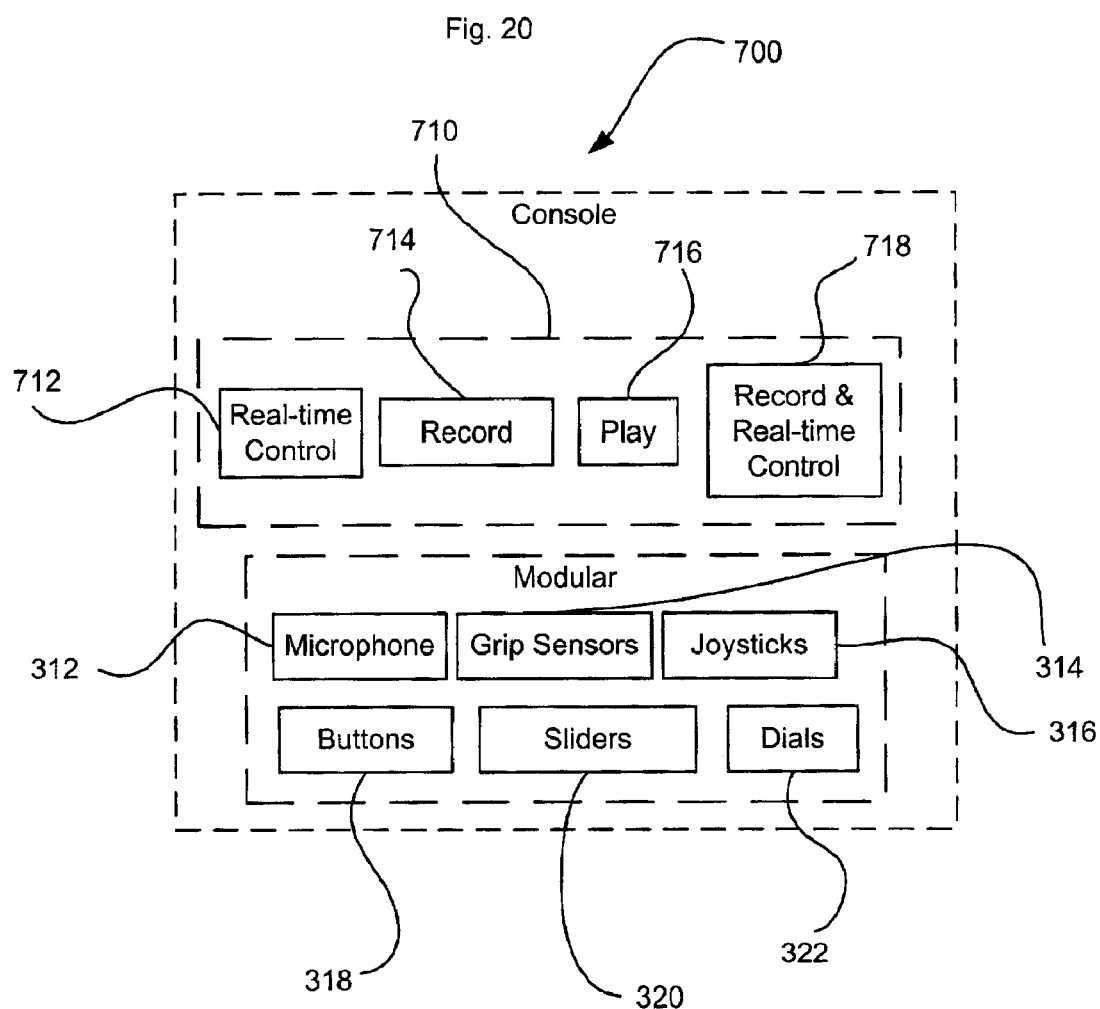
FIG. 20 is a block diagram illustrating the console with a graphical user interface.

FIG. 20 is an illustration of the console unit 700 expanded to include a graphical user interface 710. In this embodiment, the graphical user interface is shown in a monitor provided with the console to enable the user to graphically interface with the command selection as well as mode selection. In a basic form, the graphical user interface may include a selection for mode of interaction with the robotic apparatus. The mode selections include real-time control 712, record 714, play 716 or a combination mode including record and real-time control 718. In this illustration, the mode selections are shown exclusively as part of the graphical user interface. The console may also include the modular sensor components 312, 314, 316, 318, 320 and 322 as shown in FIG. 16. Accordingly, the graphical user interface expands the modes of operation of the console beyond the modular components of the sensors.

Figure 21:
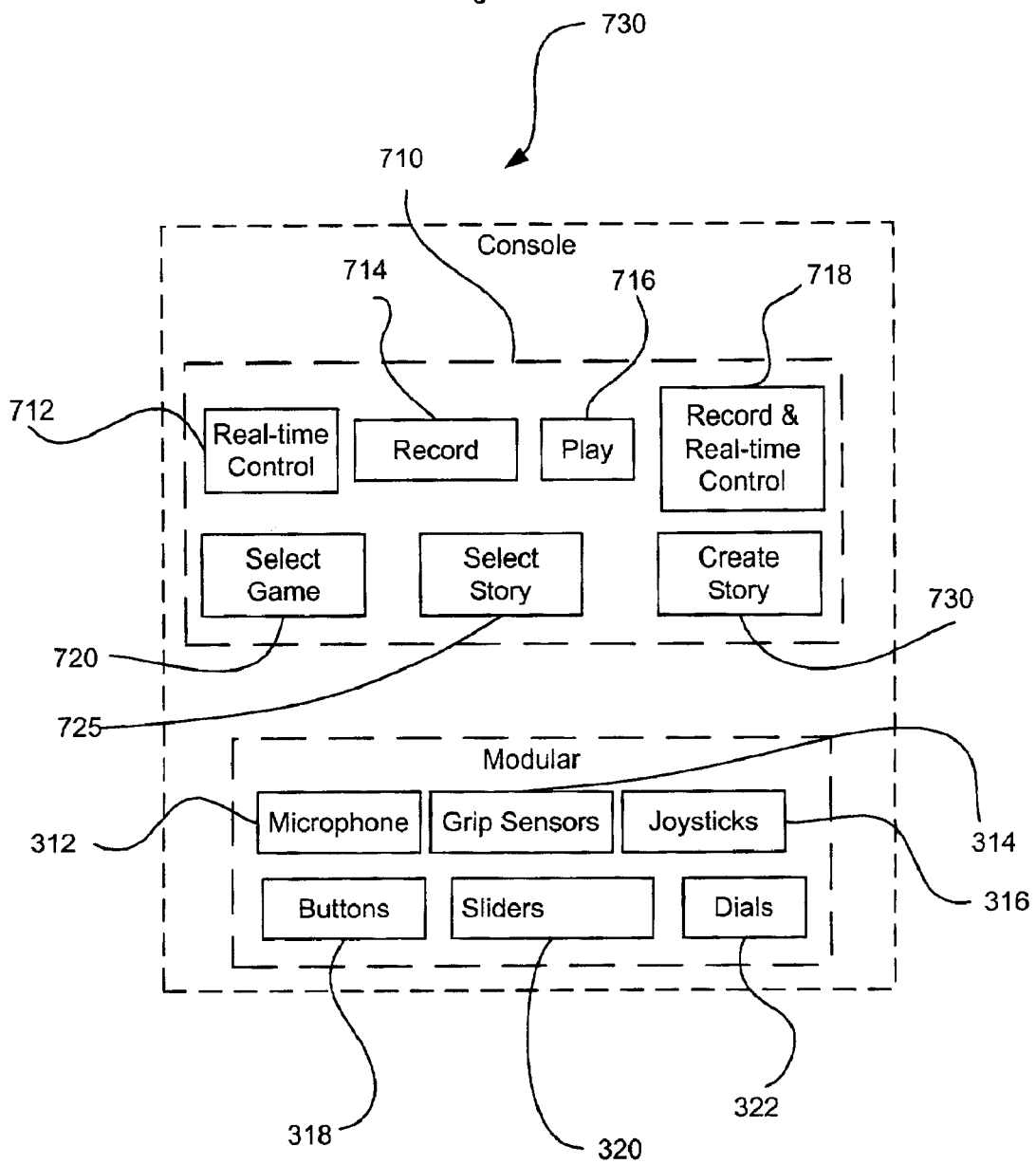
FIG. 21 is a block diagram illustrating the console with a graphical user interface.

FIG. 21 is a block diagram 730 illustrating the console together with the graphical user interface. The graphical user interface 710 on the console includes a selection for an interactive mode of operation of the system in addition to all of the functionality shown in the console unit 700 illustrated in FIG. 20. The interactive mode of operation is a dynamic mode which enables the robotic apparatus to communicate through movement and voice with a user, while enabling a user to respond through movement and voice to the robotic apparatus. The interactive modes of operation may include operation in the form of an interactive game 720, a story 725, or the ability for the user to create a game/story 730 for interaction with the robotic apparatus 10. Each of these interactive modes of operation is selectable from the graphical user interface. In this embodiment, both the console 710 and the robotic apparatus 10 include a central processing unit to accommodate the necessary memory capabilities associated with the interactive mode of operation. The selection of an interactive mode of operation is an independent selection available to a user. Accordingly, the interactive mode of operation is associated with the console unit and graphical user interface 710 and enables a user to interact with the robotic apparatus in an entertaining medium.

Figure 22:
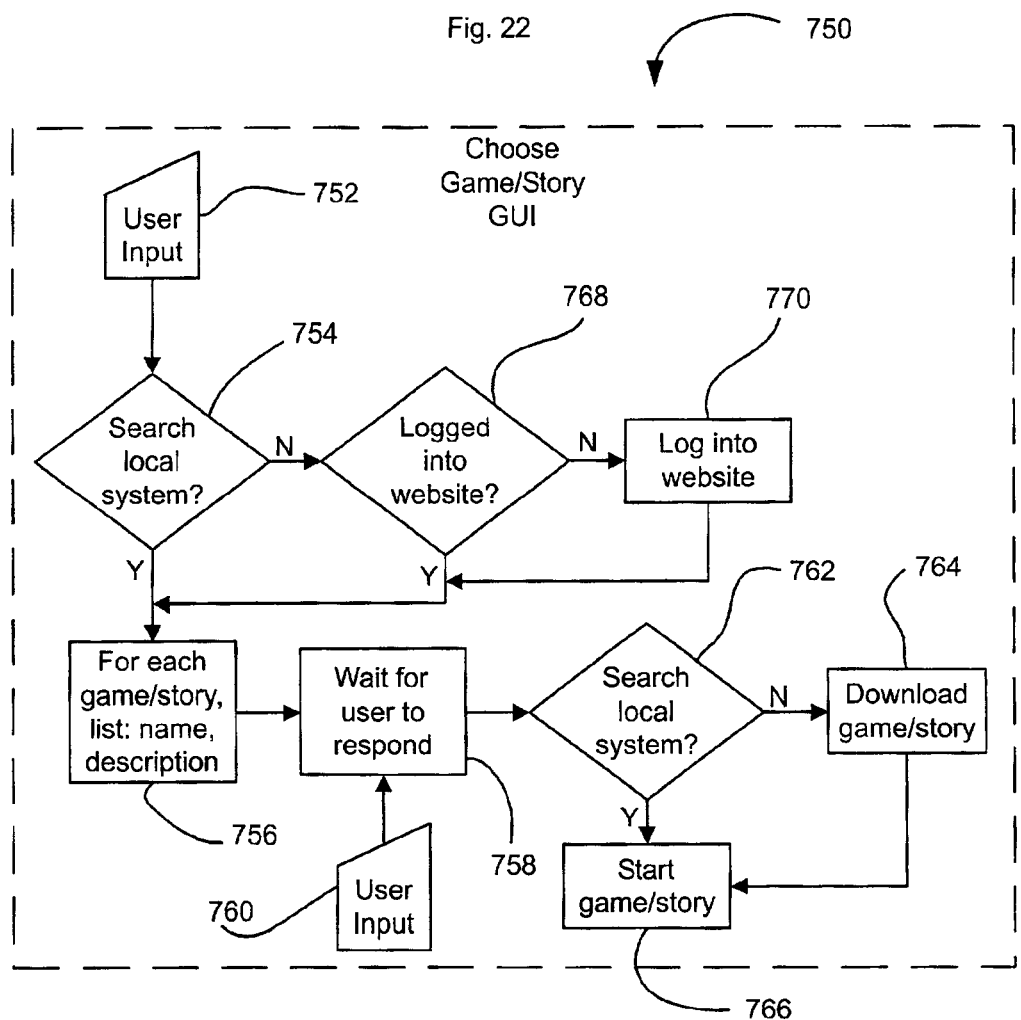
FIG. 22 is a flow chart illustrating the process of selecting an interactive game/story.

Two of the interactive modes of operation require selection of a pre-programmed game and/or story for interaction between a user and the robotic apparatus. FIG. 22 is a flow chart 750 illustrating the process of selecting a pre-programmed game and/or story. The user of the system initiates the selection by prompting the selection button on a graphical user interface 752 associated with the console apparatus. Following the initial selection 752, the user will be prompted as to whether they want to search the local system for a game and/or story they would like to use for interaction with the robotic system 754. If the user provides a positive response to the query at 754, the user will be presented with a list of games and/or storyline available for selection 756. Each game and/or storyline may be pre-programmed into the console unit. The user is provided with a name and description for each game and/or story in the menu. The system will then pause and wait 758 until the user input selects 760 a game and/or story from the menu. Following the user input, the system will query as to whether the user has submitted a search request. If the user has selected a game and/or story located on the local system, the system will then begin the game and/or story 766. In addition to downloading and playing games and/or stories with the robotic apparatus that are stored in the console, the console may be adapted to include a communication link for connection to an external server or computer, as shown in FIG. 19. In this configuration, following step 754, if the user selects not to search the local system for the stored interactive components, they are then queried to determine if the console is logged into a specific remote network 768 and if the user wants to search remotely. If the system is logged into the remote network, the user is then presented with a menu at step 756 for all pre-programmed interactive games available through both the local console and the remote network location. However, if at 768 it is determined that the console is not connected to the proper location for accessing interactive components, the user must actively log into the proper remote location 770. Thereafter, the user is presented with a menu at step 756 for all pre-programmed interactive games available through the remote network location. The system will then pause and wait 758 until the user selects a game and/or story from the menu 760. Following the user input, the system will query as to whether the user has submitted a search request. The system will then download the selected game or story 764 and subsequently begin the game or story 766. Accordingly, the graphical user interface for the interactive component enables a user to select pre-programmed games available locally or from a remote location connected to the console through the communication link. The system may automatically update the game/story selection available on the local computer each time the program is initiated or once per day both of which when there is a network connection.

Mapping

Figure 23:
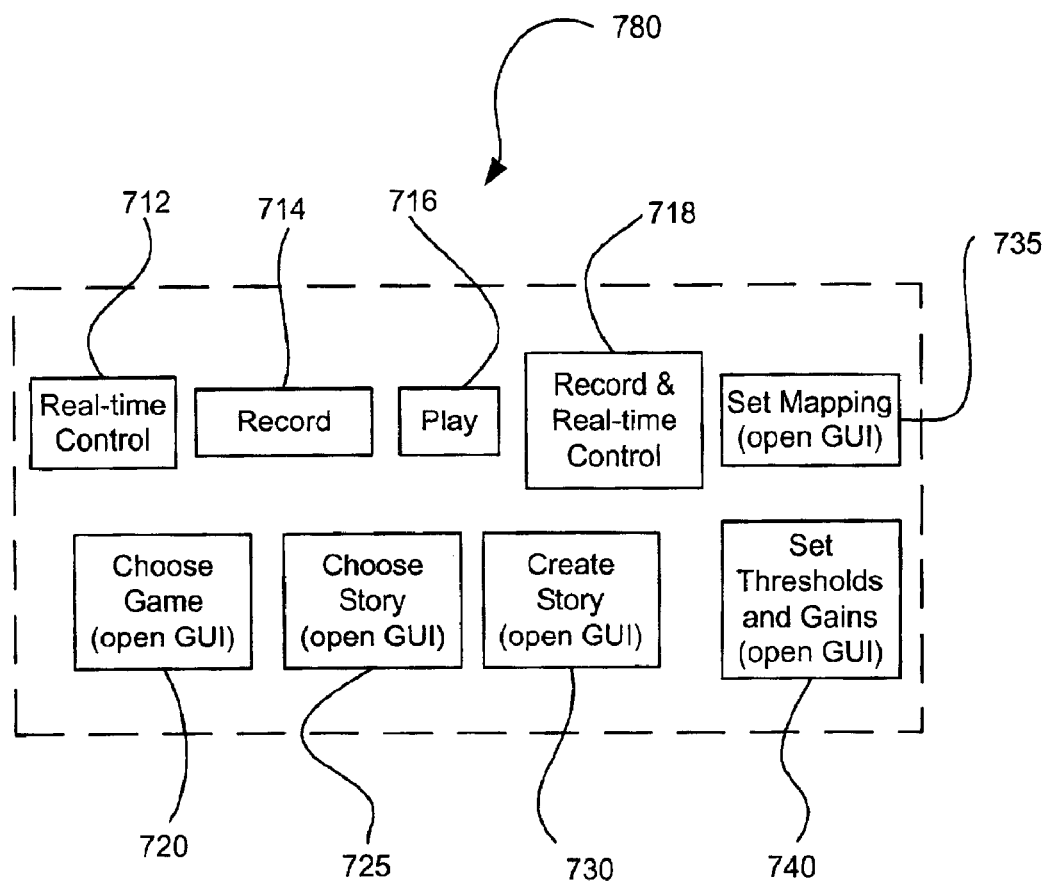
FIG. 23 is a block diagram illustrating a graphical user interface supporting a mapping selection.

In order to control the mapping between the user and the robotic apparatus, an advanced user or operator of the system, such as a therapist, educator, or a technician, must be able to select a game and/or story as well as set the mapping instructions. FIG. 23 is a block diagram 780 illustrating one embodiment of a graphical user interface supporting a mapping selection. In this diagram, the user can select the mode of operation from four modes: real-time control 712, record 714, play 716, or a combination mode including record and real-time control 718. Similarly, the graphical user interface enables the operator to select a pre-programmed game 720, select a pre-programmed story 725, or to create a new story 730. In addition to the interactive modes of operation, the graphical user interface is expanded to include links for setting the mapping of the sensors and robotic assemblies 735 and setting the thresholds and gains associated with the sensors and robotic assemblies 740. Accordingly, the expanded graphical user interface 780 enables an operator to control settings associated with the components of the robotic apparatus.

Figure 24:
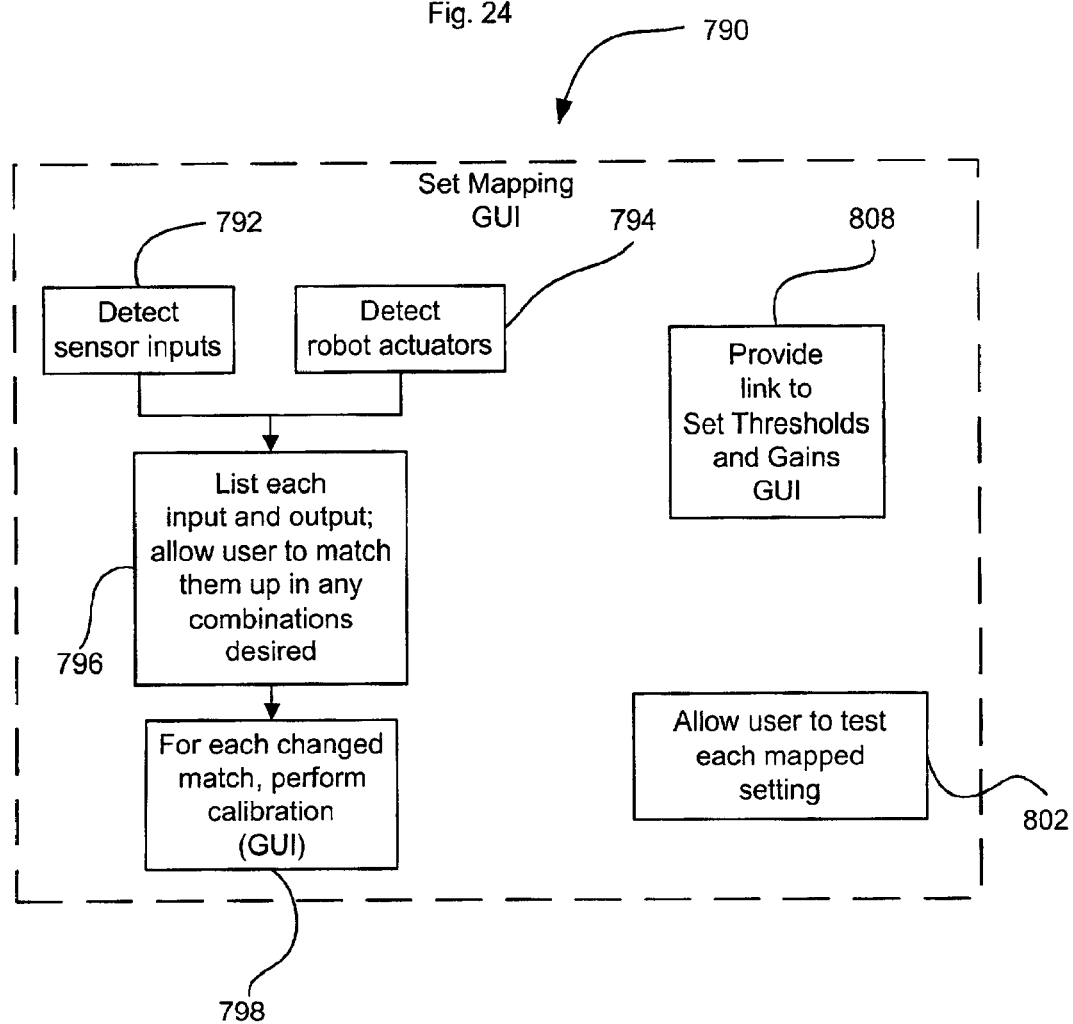
FIG. 24 is a flow diagram illustrating the process for setting mapping of sensors and actuators.
Figure 25:
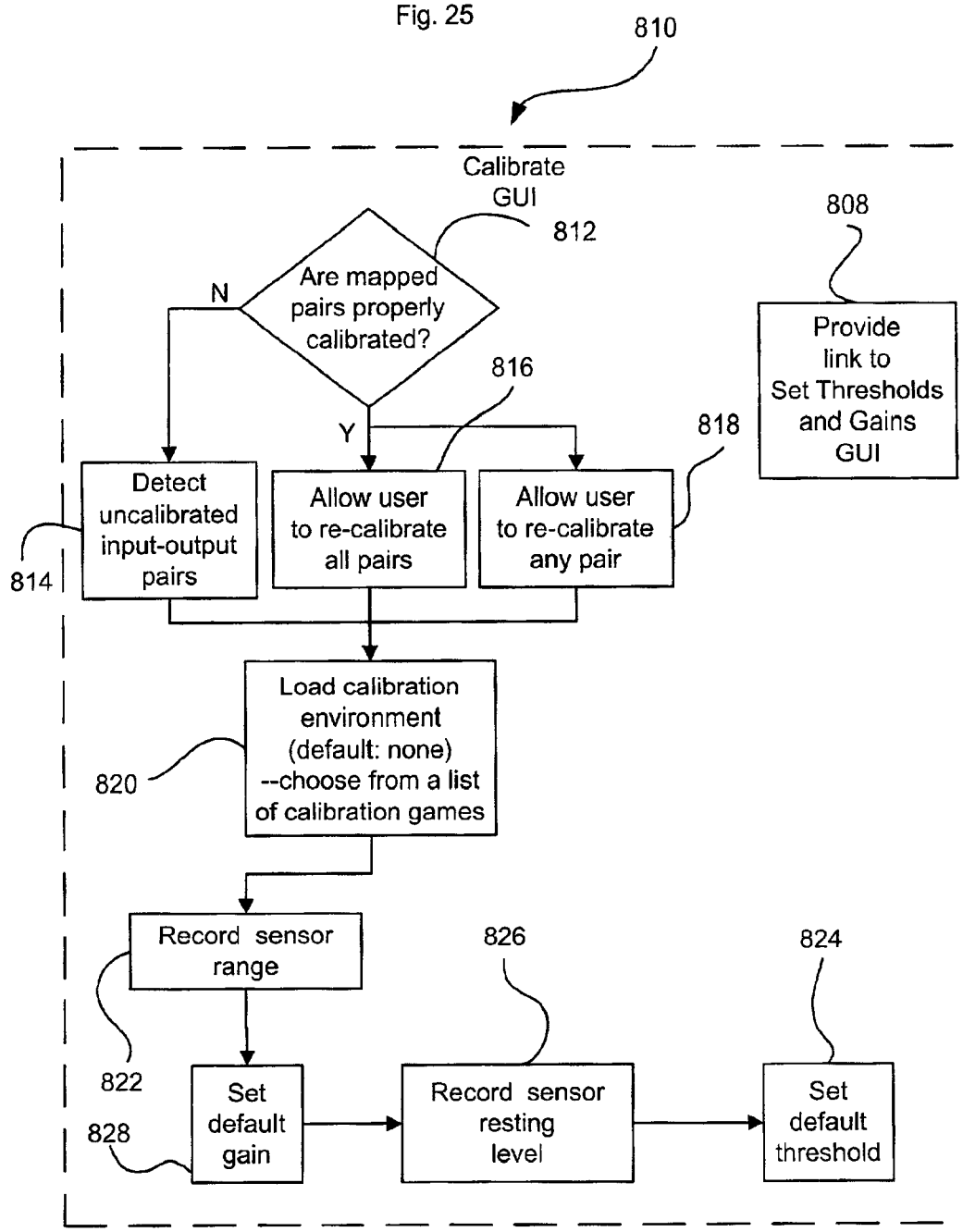
FIG. 25 is a flow diagram illustrating the process of calibrating sensors and actuators.

Mapping is the process of performing the decision-making process of what input signal is processed to which output source. Three mapping categories are (1) one-to-one, where one input sensor is linked to one output actuator, (2) one-to-many, where one input sensor is linked to many output actuators, and (3) many-to-one, where more than one sensor input is linked to a single actuator. Generally, n sensor inputs can be mapped to m actuator outputs. FIG. 24 is a flow chart 790 illustrating the process of setting the mapping through a graphical user interface. The system is prompted to detect the sensor inputs 792 from a wearable sensor network and/or sensors connected to the console, as well as to detect actuators available on the robotic apparatus 794. The sensors are referred to as input devices and the actuators are referred to as output devices. Each input device and each output device is listed on the graphical user interface, and the user and/or operator is then allowed to assign the input devices with the output devices in any arrangement desired 796. Following the assignment of inputs to outputs, the system performs a calibration of the robotic actuators and sensors 798. The process of calibrating the actuators and sensors of the robotic apparatus presents the operator with another graphical user interface, as shown in FIG. 25 and discussed below. The graphical user interface also provides the link for testing the current mapping 802 and adjusting the thresholds and gains 808 associated with the input-output mappings. Accordingly, the process of selecting a mapping of the sensors and actuators may be controlled by the user and/or operator.

The process of setting the mapping configuration includes the process of calibrating the sensors and actuators. FIG. 25 is a flow diagram 810 illustrating the process of calibrating the sensors and actuators. Upon initiating the calibration graphical user interface at 798, the system will conduct a test on the mapped sensors and actuators to determine if they are properly calibrated 812. If any of the mapped sensors and actuators are not properly calibrated, the system will detect which mapped sensors and actuators are not calibrated 814. However, if the mapped sensors and actuators are properly calibrated, the interface will allow the user to select all of the mapped sensors and actuators for re-calibration 816, or to select specifically mapped sensors and actuators for re-calibration 818. Upon selection of 814, 816 or 818, the system will load the calibration environment 820, with the default being to set no environment. The calibration environment prompts the user to make movements within a context of a game or story. Whether in an environment mode or not, the user is prompted to act in a way that each particular sensor's range is measured 822, given the sensors capabilities and the user's capabilities. If the sensor is an analog sensor, the default gain between the sensor input and actuator output can be set 828. The default gain is a linear relationship so that the maximum sensor value corresponds to the maximum actuator output value and the minimum sensor value corresponds to the minimum actuator output value. The calibration routine then records the sensor resting level 826, which are the values from the sensor while the user is not trying to activate it. This gives a reading of the sensor's noise level. The default threshold can then be set, 824. The default threshold will be a value chosen that is above the sensor's resting level and will be a function of the sensor range. The precise method of calculating the default thresholds and gains can be adjusted by the operator (not illustrated).

During the process of setting the mapping protocol, the calibration protocol, or from the main graphical user interface window, a link may be provided to a graphical user interface for the setting of thresholds and gains associated with the sensors and actuators 808. Thresholds are the defined limits upon which an actuator will move. If an input from a user is below a threshold, there is no response from the associated motor. Similarly, a gain is the relationship between the range of a sensor value to the range of output motor values for proportional sensors. FIG. 26 is a flow diagram 830 illustrating the process of setting the gains and thresholds associated with each assigned pair of actuators and sensors. As a matter of practice, the mapping configuration should be set prior to setting of the thresholds and gains associated with the mapping. The first step in FIG. 26 is for the system to detect the assignment of sensor inputs to actuator outputs 832. Each assignment is then presented to the user in a list 834. The user and/or operator may then select one or all of the following: to manually adjust the threshold setting for each assignment 836, to manually adjust the gain setting for each assignment 838, and to test each assignment for proper threshold and/or gain settings 840. In the case where more than one sensor input is mapped to an actuator output, the default relationship is that all sensor levels must be above their respective thresholds for the actuator to be activated. In addition, the minimum gain calculation from the sensor inputs will be chosen to set the magnitude of actuator output. This default relationship can be altered by the operator (not illustrated). Accordingly, the process of setting the thresholds and gains is manually adjustable by the user and/or operator of the system.

Figure 27A:
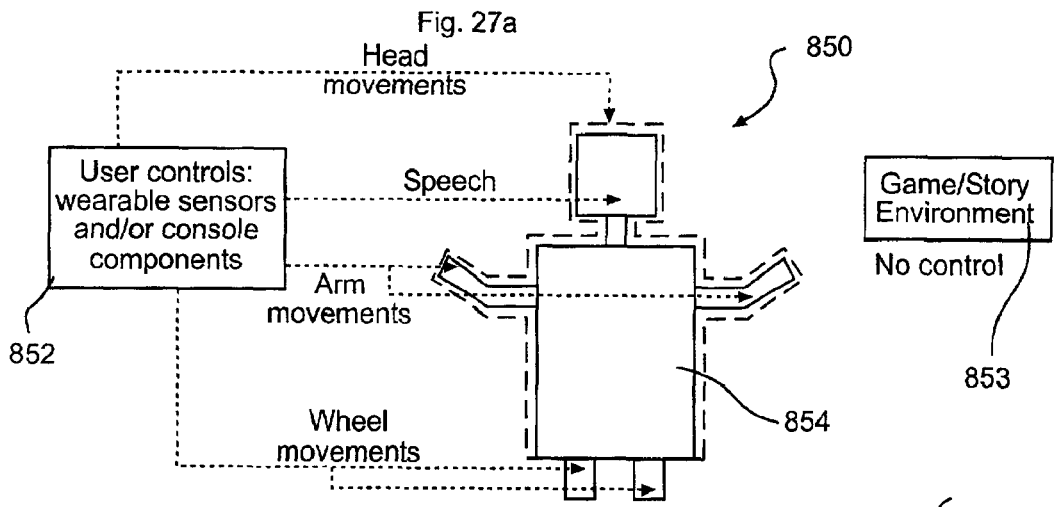
FIG. 27a is a graphical illustration of mapping in an interactive mode of operation.

FIG. 27a is a graphical illustration 850 of a basic mode of mapping between user controls 852, a game or story environment 853, and the robotic apparatus 854. The user controls may either be wireless sensors secured to the user, sensors secured to the console, or any combinations thereof. In FIG. 27a the user controls all physical, including auditory, functions of the robotic apparatus 854. The user initiates all movements of the robotic apparatus 854 through actuation of one or more of the sensors. In response to actuation of the sensor(s), the robotic apparatus actuates one or more motors, based on the set mapping, threshold, and gain settings. In this mapping example the game or story environment 853 has no control over the robot. This example is the default mapping setup, which identical to the embodiment where the user is operating the robot in real-time, record, play or record with real-time modes.

Figure 27B:
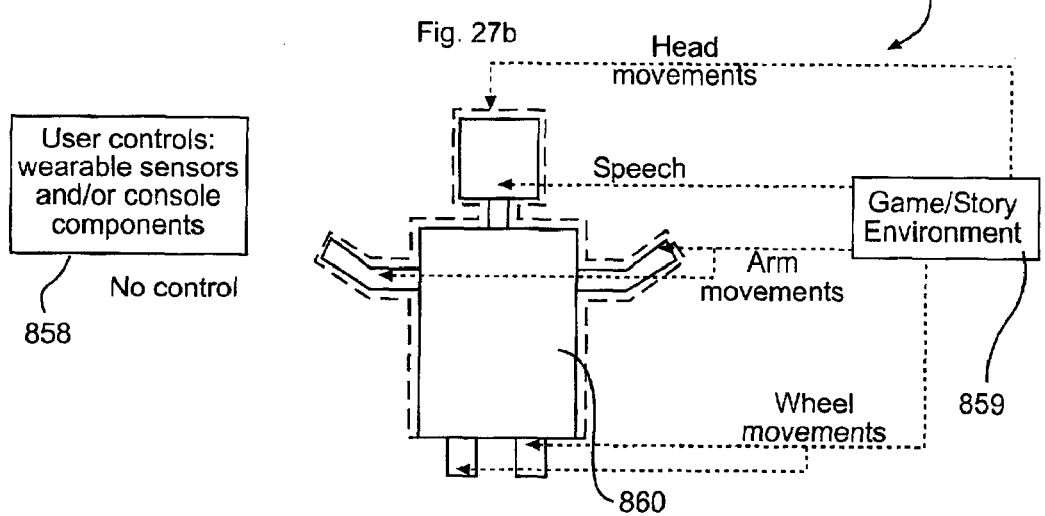
FIG. 27b is a graphical illustration of mapping in an interactive mode of operation.

FIG. 27b is a graphical illustration 856 of a second mapping example between user controls 858, a game or story environment 859, and the robotic apparatus 860. The user controls may either be wireless sensors secured to the user, sensor secured to the console, or any combinations thereof. In this mapping example the user's inputs are not mapped to the robot, therefore the user has no control whatsoever in the robot's functions. The game or story environment alone controls the robot and the user is a passive observer. Accordingly, in this mode of operation, the game and/or story is in control of movement of the specified body parts and associated motors of the robotic apparatus.

Figure 27C:
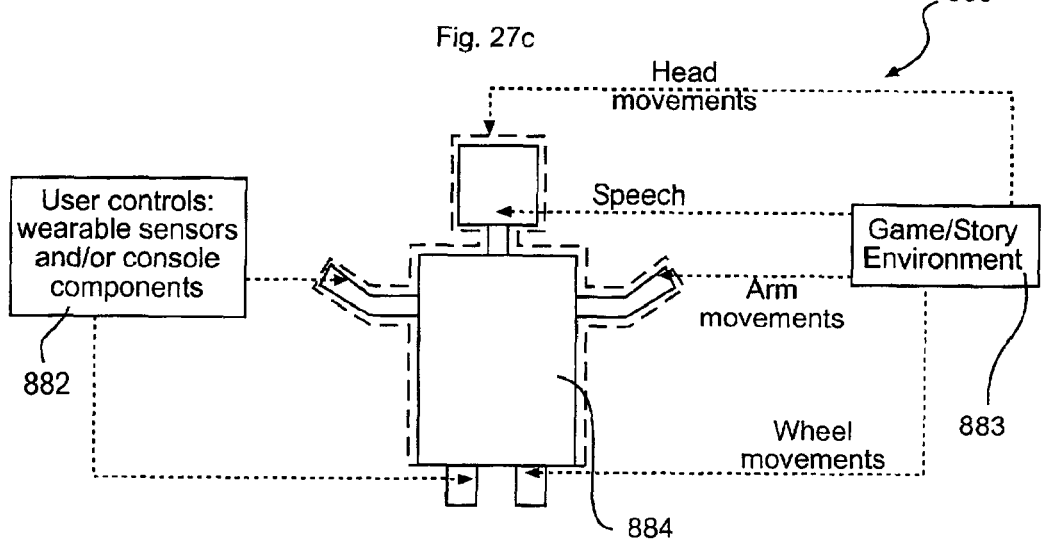
FIG. 27c is a graphical illustration of mapping in an interactive mode of operation.

FIG. 27c is a graphical illustration 880 of a third mapping example between user controls 882, a game or story environment 883, and the robotic apparatus 884, wherein the control of the robot is shared between the user and the game/story environment. In particular, the game/story environment controls the robot's speaker output, head movements, left arm, and left wheel. This mapping example can be used to play simple games, such as telling the user to replicate the robot's left arm and wheel movements by activating sensors to control the robot's right arm and wheel movements. A second simple game example is to tell the user to execute a movement, then the game environment mirrors the movements when they are correct. Accordingly, in this mode of operation, the game/story and the user each have limited control of the physical controls of the robotic apparatus and the game/story controls the auditory functioning.

Figure 28:
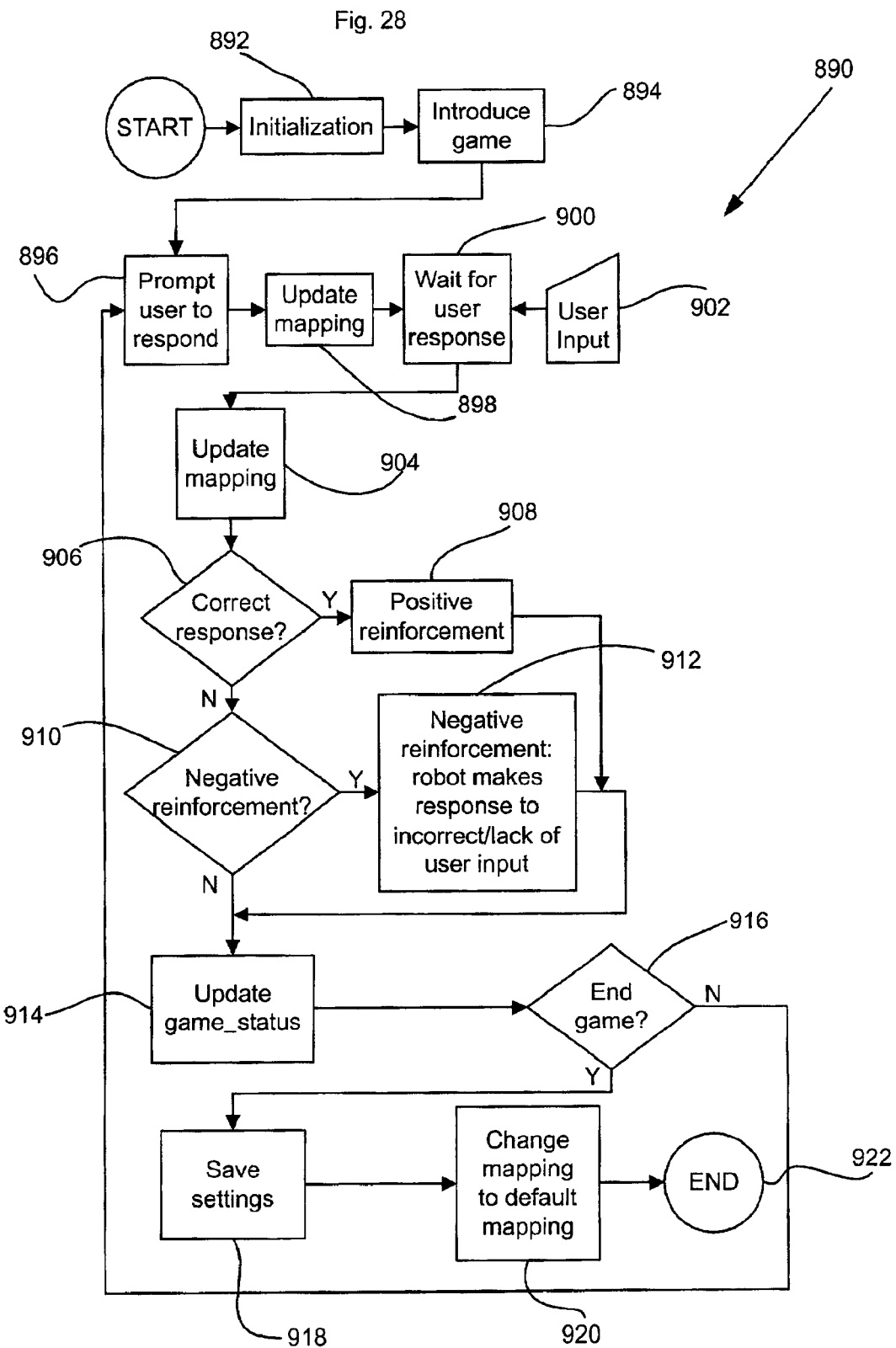
FIG. 28 is a flow chart of the mapping process for an interactive component.

A more complicated form of interaction is provided by a game or story environment in which the input-output mappings change over time, or dynamic mapping. FIG. 28 is a flow chart 890 illustrating the general outline of events that are to occur in such an interactive game or story. When the user completes the process of selecting a game or story at step 766 in FIG. 21, the game or story is initialized 892. During initialization the mapping is set so that the game/story has complete control of the robot, as shown in FIG. 27b. The parameters of the game/story are also set in initialization 892, including the form of positive reinforcement, whether negative reinforcement will be provided, the number of attempts the user has to make a response to a given prompt, and the condition for ending the game or story. While the game or story has complete control of the robot, the robot introduces the game or story to the user 894. The user is then prompted to perform a certain action 896 and thereafter the mapping is updated 898 to allow the user some control of the robot, as in mapping example 880 (FIG. 27c) or complete control of the robot, as in mapping example 850 (FIG. 27a). The system then waits for the user's response 900. Following input from the user 902, the system updates the mapping to remove some/all of the robot control from the user 904. The system determines if the input from the user was a correct response 906. If the input from the user was a correct response, the robotic apparatus responds with actuation of the mapped motor as a form of positive reinforcement to the user 908. However, if at step 906, it is determine that the user response was incorrect, the system must then determine if negative reinforcement should be provided to the user 910. An incorrect response could be (a) a lack of response, (b) a response that was correct but below threshold, (c) an incorrect sensor activation, (d) and incorrect auditory signal, or any combinations thereof. If the interactive game or story is programmed to provide negative reinforcement to the user in the case of an incorrect response, negative reinforcement may be provided 912, wherein the robotic provides a visual or auditory response to the user indicative of an incorrect input or a lack of input. Following the positive reinforcement at 908, the negative reinforcement at 910, or the determination that a negative reinforcement is not warranted, the status of the game or story is updated 914. The update could be to repeat the last step of the game or story (especially after an incorrect response) or to proceed in the game or story. The system then determines whether the game or story has reached the end 916. The ending condition was set in the initialization step 892 and could be based on the duration, number of trials, number of correct or incorrect trials, or any other ending criterion. If the game or story has not met this condition, the game or story returns to step 896 to prompt the user for a response. However, if at step 916 it is determined that the user has reached the end of the game or story, the settings for the environment are saved 918, the mapping of the sensors and associated motors are changed to their default values 920, and the game or story is concluded 922. The mapping is dynamic because it can change to any configuration imagined by the game/story environment software at the two junctures 898 and 904 in the game/story 890, which is every time before and after the user is given a chance to respond to a prompt.

In addition to selecting interactive stories or games from a library of pre-programmed stories and games, the user may also create a story and/or game. This exercise may be conducted by a user, regardless of their level of expertise with game or story authoring. In addition, interactive environments can be developed by therapists, educators, or other expert operators for developing interactive therapy and/or educational environments. As shown in FIG. 21, the operator can access the means for creating a game or story 730 given this graphical user interface 710.

Figure 29:
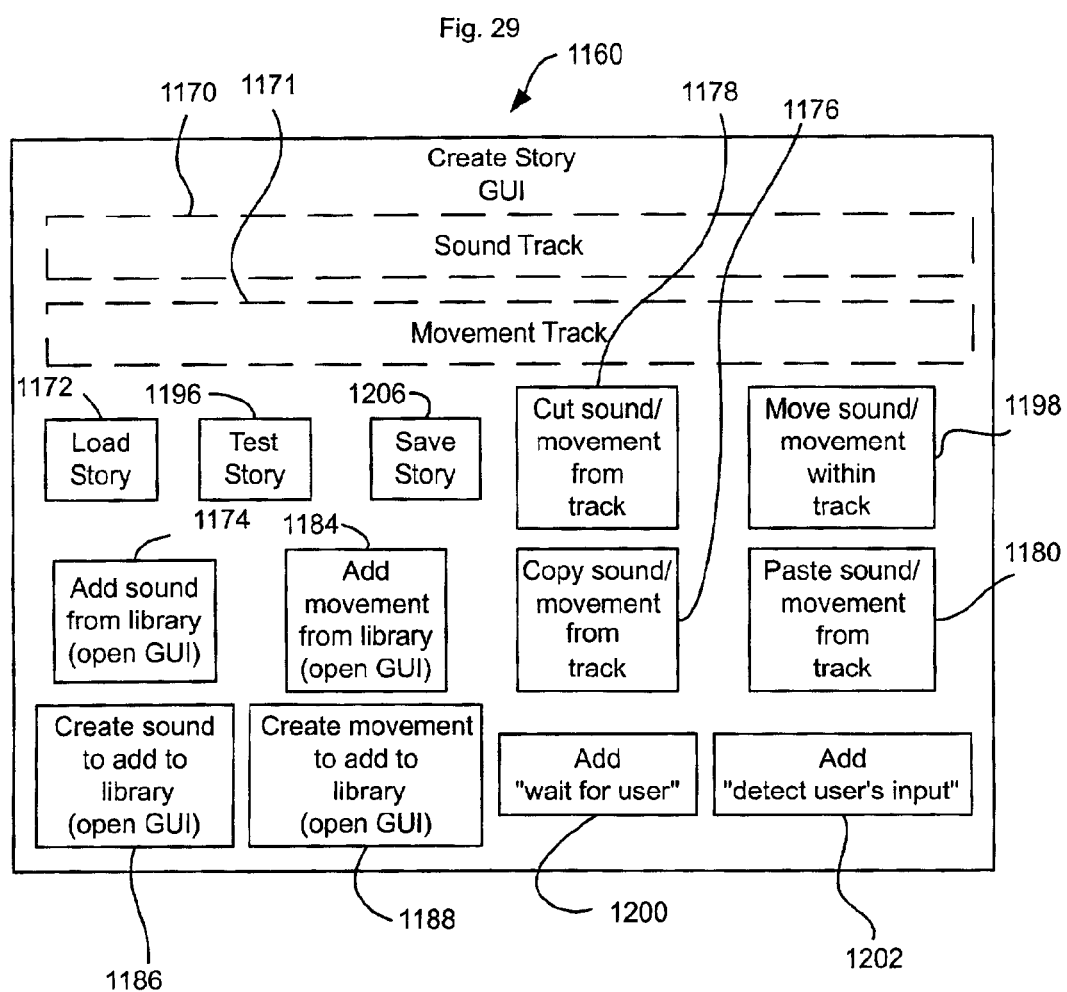
FIG. 29 is a graphical illustration for creating an interactive story.

A user, therapist, educator, programmer, technician, or other type of expert operator may take advantage of the capabilities of the system which are designed to enable then to create customize games and/or stories. FIG. 29 is an example of one form of a graphical user interface 1160 presented to the user upon selection of the link 730 in the console design shown in FIGS. 21 and 23. The graphical user interface 1160 has two tracks to be edited. The first component is a sound track 1170 for embedding sound inputs into the game and/or story, and the second component is a movement track 1171 for embedding movement of select assemblies into the game and/or story. Each of these tracks 1170 and 1171 are graphical representations of time; the remaining components of the graphical user interface 1160 can be utilized to fill these tracks with sound and movement signals that have been created in a pre-existing sound library 1174 and a pre-existing movement library. These links open another graphical user interface, in which the user can choose the sound or movement clip to add to the sound track 1170 or movement track 1171. Furthermore, the user can create a new sound to add to the library by using link 1186. This link opens the graphical user interface 710, illustrated in FIG. 20, to allow the user to record a sound and save it in the library. Likewise, the user can create a new movement sequence, using a microphone mapped to the robot auditory output, to add to the library by using link 1188. This link opens the graphical user interface 710, illustrated in FIG. 20, to allow the user to record a movement sequence, using wearable sensors and/or sensors on a console that are mapped to the robot's actuators, and save it in the library. The sound track 1170 and movement track 1171 can be edited by cutting 1178, copying 1176, moving 1198, and pasting sound or movement sequences that have been previously added into the tracks. The user can also drag and drop movement and sound data (not shown). The user can also create interactive components to the game or story by adding a section of time in the sound track 1170 and/or movement track 1171 to wait for the user to make a sound or movement stimulus 1200. Likewise, the user can create a section of time where the user input is to be detected 1202 by the game or story environment. At any point subsequent to the creation of a game/story, the user may also select to test the created game/story 1196 as a review of the auditory and physical movements embedded in the game/story. Following creation of the game/story, or at any time in the process of creating the game/story the user can select to save the game/story 1206. The illustrated graphical user interface is one example of a simple and intuitive means for creating a game or story that is flexible enough to make very simple or intricate interactive games or stories. By taking advantage of the available customization features, the user may select among each of the links in the graphical user interface to create a unique game/story. This graphical user interface also enables a operator, either locally present at the session or monitoring the session from a remote location, to virtually control the physical and auditory functions of the robotic apparatus and also create a unique game/story or take advantage of the other features of the system, while locally present or from a remote location, as shall be described in greater detail below. Accordingly, the graphical user interface provides an array of selections for enabling and assisting a user in creating a unique game or story.

Figure 30:
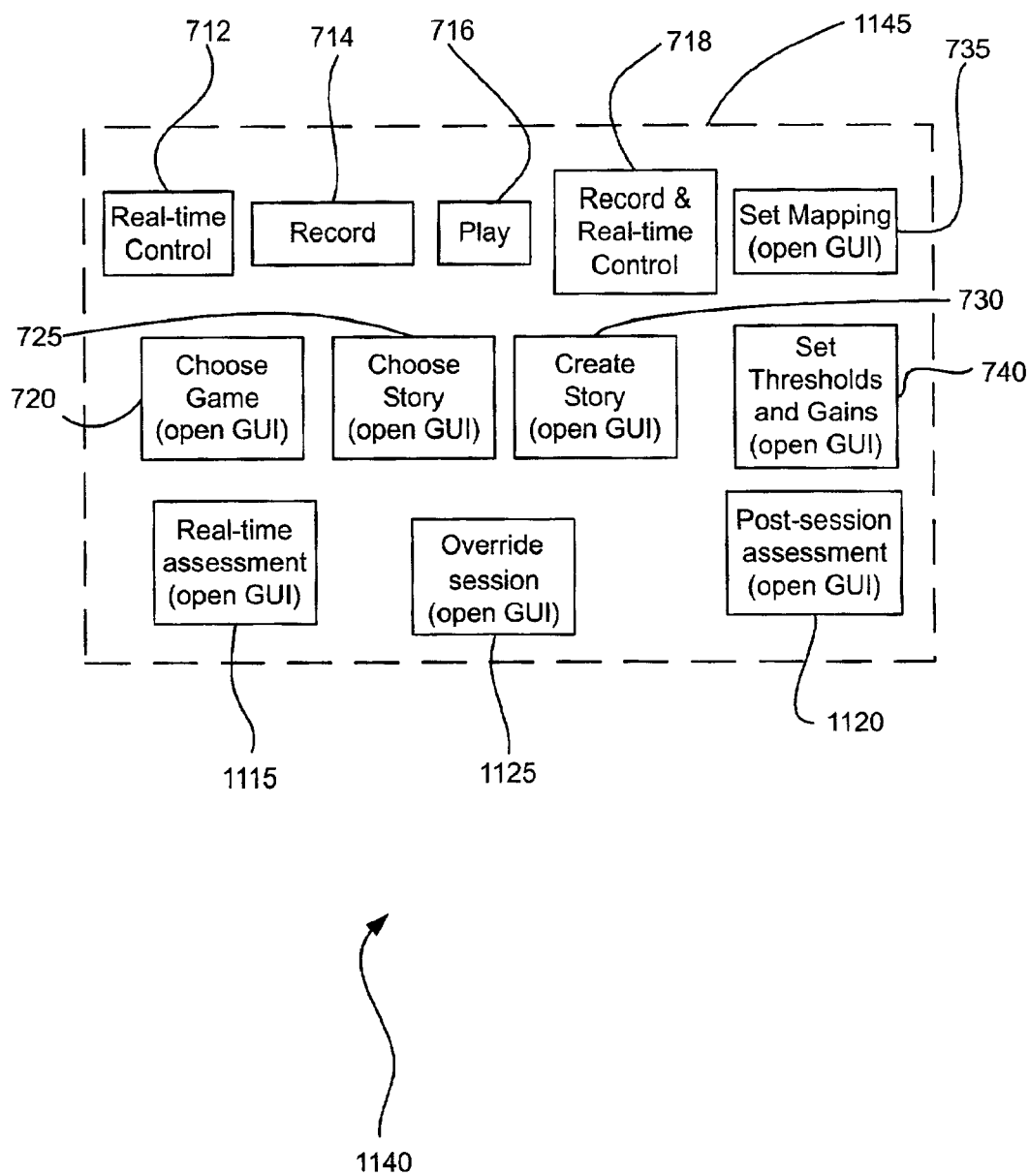
FIG. 30 is a block diagram illustrating the console with a graphical user interface.

FIG. 23 is an illustration of a console design for an advanced user seeking to expand the capabilities of the robotic apparatus by creating a game/story for interaction with the robot, in addition to playing existing games and stories and using the basic capabilities of controlling the robot in record, play and real-time modes. However, in the case where a operator is in control of the robotic apparatus from a local or remote location, either for assessment or programming purposes, the graphical user interface may be further expanded to enhance use of these functions. As shown in FIG. 19, the operator may monitor and modify the user's session with the robotic apparatus 10 and its sensors through the local PC 680, the remote PC 690, or the console 660. FIG. 30 is a block diagram 1140 illustrating the graphical user interface of the console unit for a operator seeking to use advanced functions of the robotic system either locally or from a remote location. The graphical user interface 1145 is similar to the interface shown in FIG. 23. In this embodiment, the user can select the mode of operation from four modes: real-time control 712, record 714, play 716, or a combination mode including record and real-time control 718. Similarly, the graphical user interface enables the operator to select a pre-programmed game 720, select a pre-programmed story 725, or create a new story 730. The graphical user interface also includes links for setting mapping of the sensors and robotic assemblies 735 and setting the thresholds and gains associated with the sensors and robotic assemblies 740. In addition, the graphical user interface 1145 includes additional links for enabling the advanced functionality. The operator may select from the following links: to monitor the session of the user in real-time 1115, to acquire data from a session following completion of the session 1120, or to over-ride a session 1125. Accordingly, the expanded graphical user interface 1145 enables a therapist, educator or similar operator to take advantage of the enhanced capabilities of the robotic system.

Figure 31:
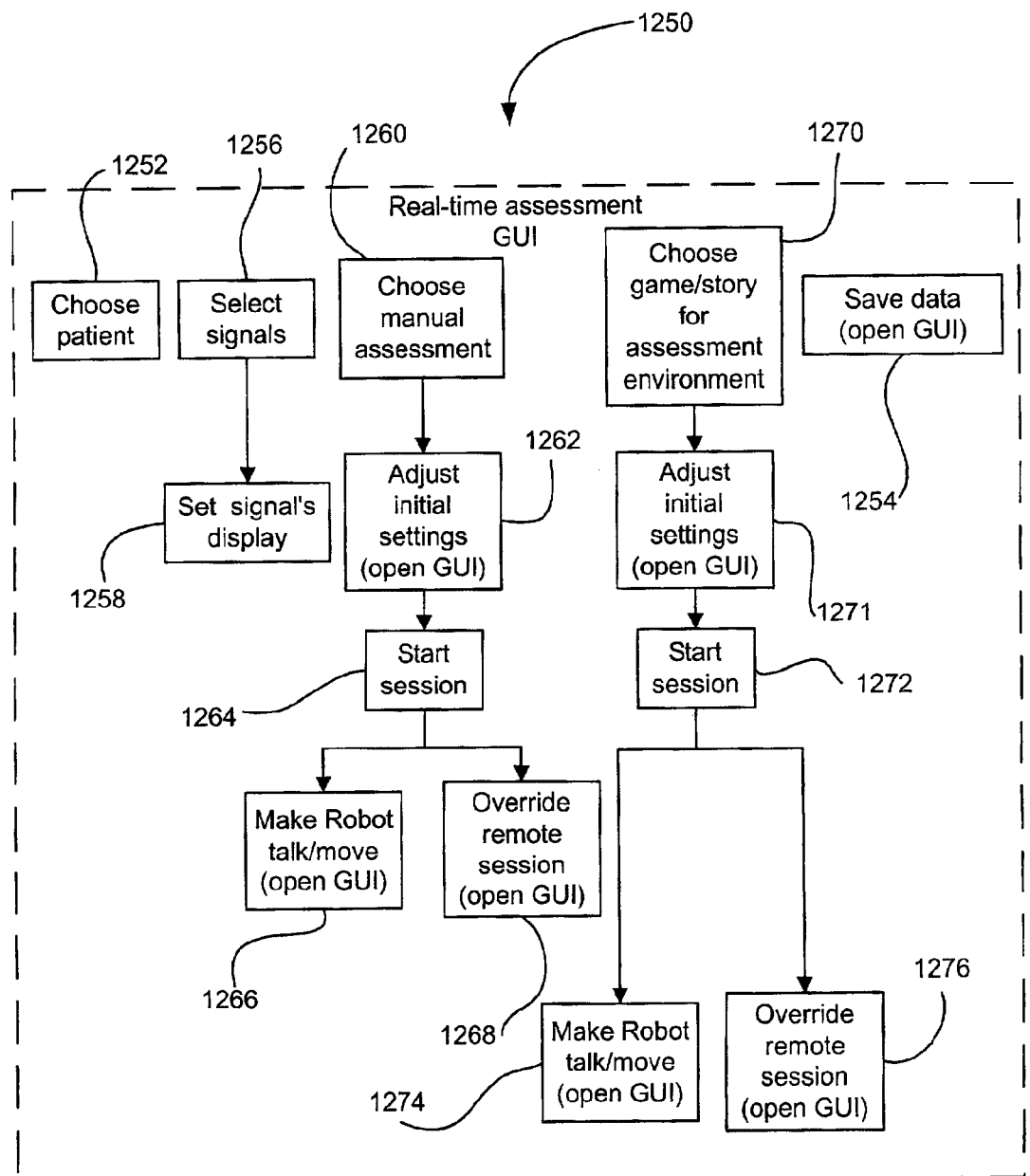
FIG. 31 is a flow chart for conducting real-time assessment of a session with the robotic apparatus.

As shown in FIG. 30, an operator monitoring a session locally or from a remote location may have expanded capabilities from that of a patient, student, or similar user. FIG. 31 is a graphical user interface 1250 illustrating the process of assessing the progress of a patient interacting with the robotic apparatus in real-time control. The first step in the assessment process is to select the patient 1252. The operator may select at any time in the session to save the patient data 1254 for subsequent review and analysis. Following the selection of the patient, the operator may select the signals 1256 the signals associated with the sensors and associated motors for online view. For each signal chosen, a window will open up to display the signal's activity. The operator can then choose to alter the signal's display 1258 at any time. The operator may select to conduct a manual assessment of the therapy of the patient interacting with the robotic apparatus 1260. A manual assessment is one in which the operator communicates directly with the user and/or manipulates the robot's functioning to prompt the user to perform the requested activities. The operator can choose to adjust the manual settings of the sensors and associated motors 1262, then the operator can choose to start the session at any time 1264. During the session, the operator can select to have the robotic apparatus initiate auditory signals and/or physical movement of specific motors 1266. In addition, the operator can select a graphical user interface 1268 to intervene and override a remote session. In addition to performing a manual assessment 1256, the operator may also select to assess the user through interaction with a pre-programmed game/story 1270. In this type of assessment, the user is prompted to perform requested activities by the interactive environment. Upon selection of a game/story, the operator may select a graphical user interface 1271 to adjust the initial settings of the sensors and motors. At any time following the selection of the game/story, the operator can select to start the session 1272. The game/story select will initiate movement of the robotic apparatus, with input from the user in communication with the sensors also potentially causing movement of the robotic apparatus 1274. Depending on how the interactive environment is programmed, the operator may be required to or may have the option to adjust any of the environment's parameters. Whether the operator is requested or required to adjust the game or story by the assessment program, the operator may select a graphical user interface 1276 to override the controls of the system transmitted to the robotic apparatus by the protocols of the programmed game/story environment. In addition, the operator can directly make the robot talk or move 1274 at any time during the programmed game/story environment. At any time in the assessment process, the operator may open a graphical user interface 1254 to save the session data. Accordingly, the operator has a plurality of controls for monitoring a session of the robotic apparatus with a patient either locally or remotely.

Figure 32:
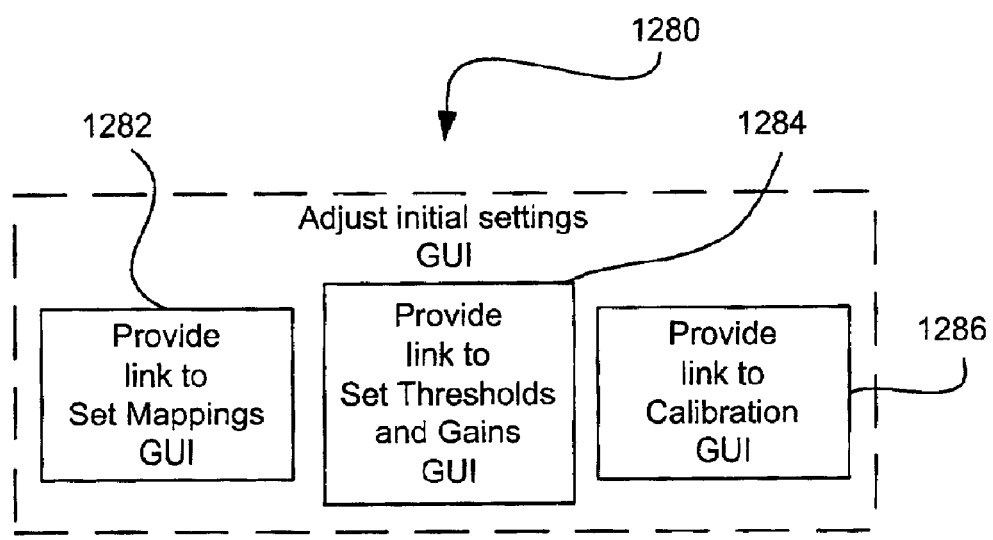
FIG. 32 is a graphical illustration for adjusting initial settings.

As shown in FIG. 31, the operator may make adjustments to the sensors and motors of the robotic apparatus prior to or during a session. FIG. 32 is an illustration of a graphical user interface 1280 presented to the user upon selection of link 1262 or link 1271 in FIG. 31. This graphical user interface 1280 provides the operator the opportunity to adjust the settings governing the relationship between the robotic apparatus, the user, and the assessment environment. In particular, the operator is presented with a link to set mapping protocols between the sensors and motors 1282, a link to set thresholds and gains associated with the sensors and motors 1284, and a link to calibrate the sensors and motors 1286. Each of these links are discussed above and shown in the associated drawing figures.

Figure 33:
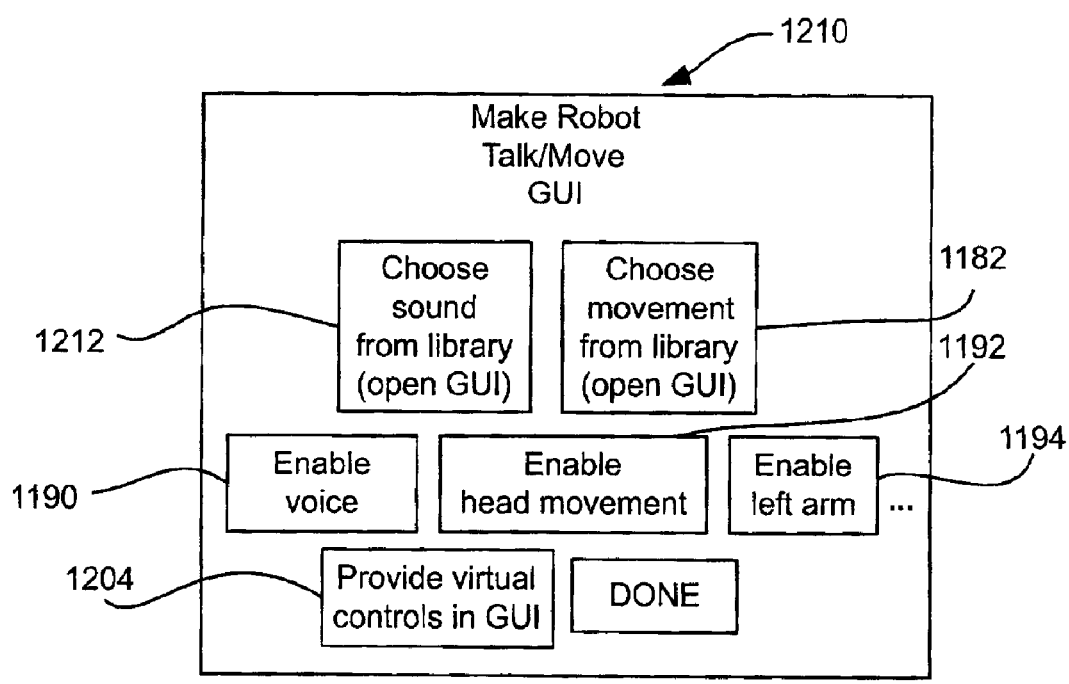
FIG. 33 is a graphical illustration for embedding sound and movement into an interactive game/story.

During the assessment session, the operator can make the robot talk or move at any time. This may be the primary mode of context for the manual assessment, where the operator chooses link 1266 in FIG. 31 to make the robot talk or move. Alternatively, the operator can interrupt a an assessment embedded in a game or story environment by choosing link 1274 in FIG. 31 to make the robot talk or move. Either link opens a graphical user interface 1210, illustrated in FIG. 33, to control the robot. The operator can then control the robot's sound by choosing sounds stored in a library 1212, which then opens another graphical user interface to choose the desired sound (not illustrated). Likewise, the operator can then control the robot's sound by choosing sounds stored in a library 1182, which then opens another graphical user interface to choose the desired sound (not illustrated). Alternative to choosing sounds or movements from stored libraries, the operator can directly enable the robot's voice in real time 1190 or enable individual robot movements in real time. Specifically, the operator can enable the head movement 1192 or left arm movement 1194. In general, all detected possible robotic movements are present presented in a graphical user interface with individual controls such as links 1192 and 1194. When the operator activates sound and movement controls 1190, 1192, and 1194, the currently set mappings that are affected by the given controls are temporarily relinquished, until the operator has completed the given intervention. The operator can also select to make the robot talk or move in real-time in a more complicated fashion, so that the operator controls more than one robotic action at a time. The operator chooses the link to provide virtual controls in a graphical user interface 1204. The resulting graphical user interface contains a set of virtual controls to allow the operator control one, many, or all of the robotic functions at a time. While the operator is controlling the robot, some or all of the currently set mappings are temporarily relinquished, until the operator has completed the given intervention. Accordingly, the graphical user interface 1210 provides the operator with additional controls for directly controlling the robot in any manner chosen at any time during a real-time assessment session.

Figure 34:
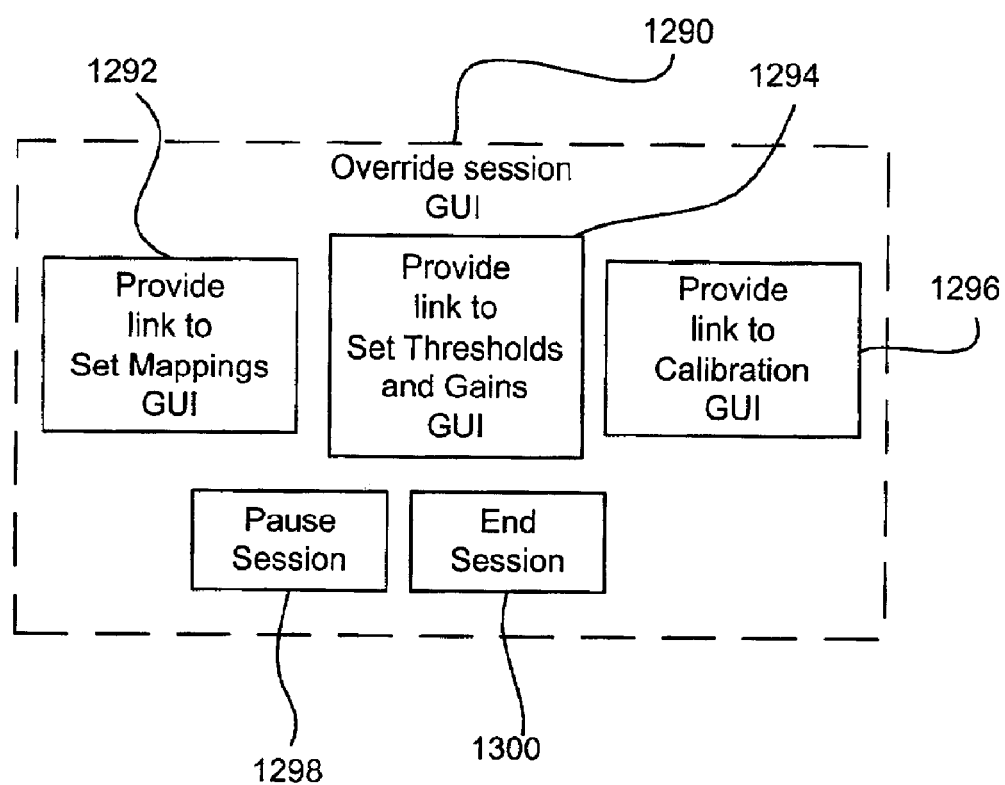
FIG. 34 is a graphical illustration for overriding a session.

In addition to adjusting the session's settings prior to starting the session and directly making the robot talk or move, the operator is provided with the capability of overriding the session at any point in time by links 1266 and 1276 in FIG. 31 and link 1125 in FIG. 30. The purpose overriding of a session in progress is to enable a operator to make adjustments to the mapping, thresholds, gains and/or calibrations in real-time. There are numerous reasons for overriding a session to adjust these protocols, which need to be available to such an expert operator. Such adjustments may be based upon improper settings that are apparent during a session. Alternatively, the operator may determine that the patient is capable of increased thresholds or that the patient is not capable of performing under the defined thresholds. Accordingly, the availability of the override is to enable a operator to make their own judgment as to the progress of the patient and the session, and the specific circumstances present. FIG. 34 is an illustration of a graphical user interface 1290 presented to the operator upon selection of link 1125 in FIG. 30, link 1268, or link 1276 in FIG. 31. The operator is presented with a link to set mapping protocols between the sensors and motors 1292, a link to set thresholds and gains associated with the sensors and motors 1294, and a link to calibrate the sensors and motors 1296. Each of these links are discussed above and shown in the associated drawing figures. In addition, the operator is presented with a link to pause the session 1298. This may be necessary for a variety of reasons. For example, the user may need to take a break, or the operator may need to communicate directly with the patient without the presence of the robotic apparatus. Alternatively, for a variety of reasons, the operator may determine that a session should end 1300, and/or whether or not the patient has completed the protocols for an entire session. Accordingly, the graphical user interface 1290 provides the operator with additional controls for actually pausing or ending a session prematurely.

Figure 35:
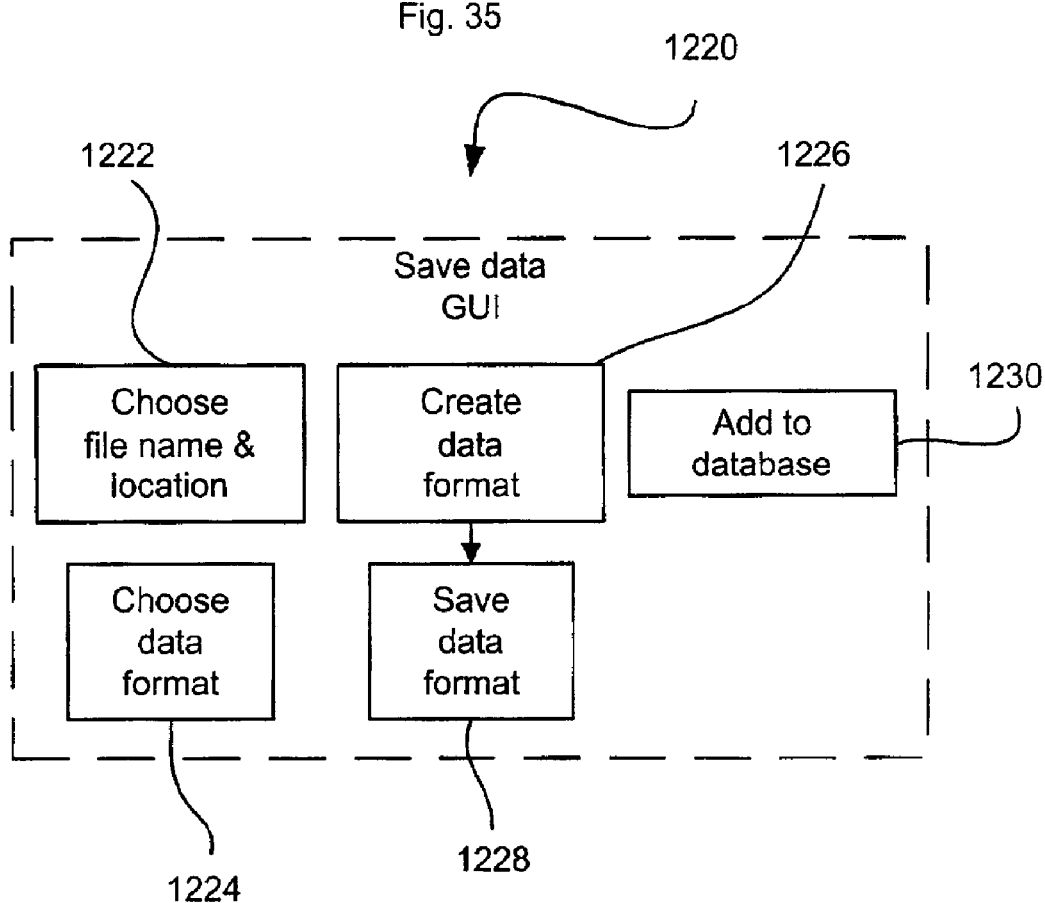
FIG. 35 is a graphical illustration for saving an interactive game/story created.

Following the start of the assessment session, or at any time in the process of performing the real-time assessment, operator can select to save the session 1254. This enables the operator to save a record of all assessment environment settings and user activities, registered by the given sensors, during the assessment session. Upon selecting link 1254 in FIG. 31, the operator is presented with the graphical user interface 1220 as shown in FIG. 35. The user can select a name for a file for the session's record as well as a location within a processing unit for saving the file 1222. Similarly, the user can select a format in which the file data will be saved 1224. The file contains sensor signal data associated with the session, a comparison of the sensor data to specific thresholds desired, the requested activities during a session, and the user's performance. Each set of quantitative data, from a sensor, a user, a session, etc, can be presented as individual data points in a graph, summary data points (mean, standard deviation, etc.) in a graph, data entries in a table, etc. Moreover, each set of data can be set to not be presented at all. The presentation of all data within a file is saved in a data format. If the file format which the user is seeking is not available, the user may select to create a format of the file data format 1226, and to save that data format 1228. The user may select a database 1230 and save the file to the chosen database so that the given file is saved in the database, in addition to or instead of saving the data in an individual file. Accordingly, the graphical user interface 1220 is presented to the user following the selection to save the assessment session data in any name, location and/or format desired.

Figure 36:
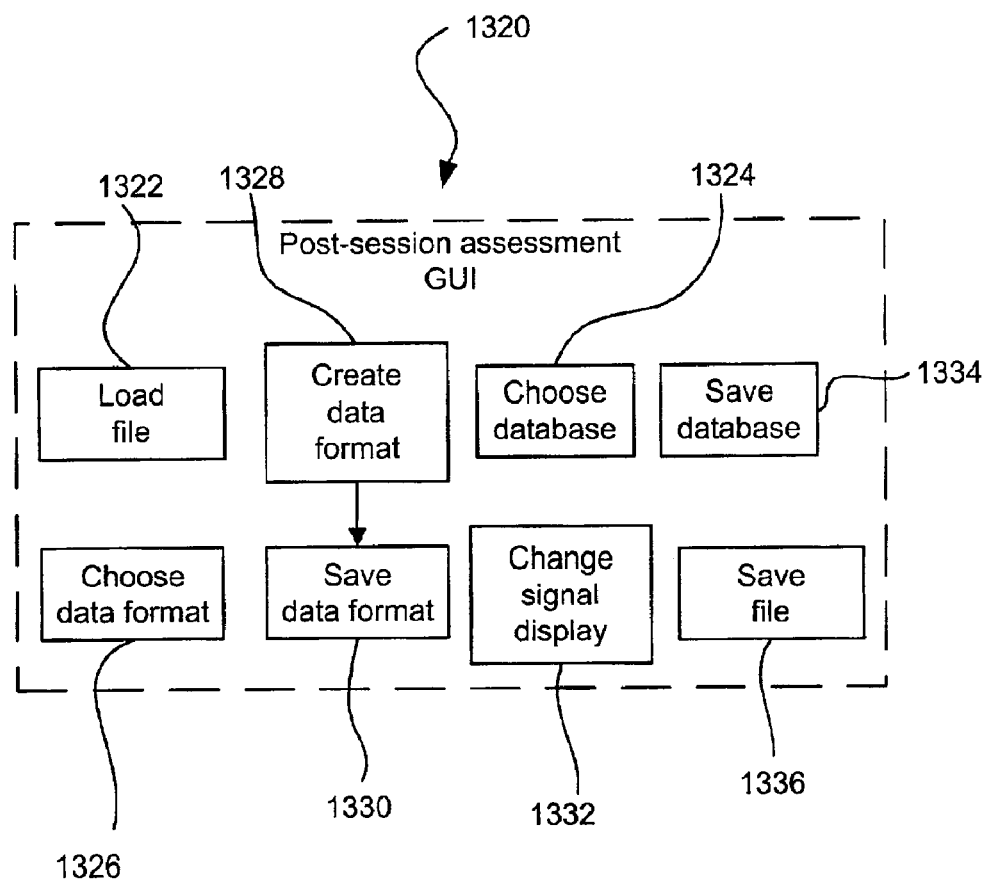
FIG. 36 is a graphical illustration for conducting post-session assessment of a session with the robotic apparatus.

The operator may monitor a session in real-time or they may monitor session data at a time subsequent to a session, either locally or from a remote location. The operator can select a graphical user interface 1120 to acquire the data subsequent to the session. Similarly, if the operator is present locally they can select a graphical user interface 1320 to assess the data from a specific session. Link 1120 in FIG. 30 will present the operator with the graphical user interface 1320 in FIG. 36. Upon selecting this graphical user interface, the operator is presented with a menu of options. They may load a specific file from 1322 or they may select a specific database 1324 for either retrieving or saving file information. Either selection enables the operator to retrieve records from a particular user, from either a single session or a multitude of sessions. The presentation of all data within a file or database is saved in a data format. Data will be presented in a default format set for the given operator and/or given user's data. Data formats can be chosen from a selection of pre-programmed formats 1326. The operator may select an alternative data format 1326, or they may create a format for the data 1328, based on altering a previous format or creating an entirely new format, and save the format to the processing unit 1330. The current data format can be adjusted by individually adjusting each signal's display 1332. Any alterations to the individual file's settings can be subsequently saved by choosing link 1336. Likewise, any alterations to the chosen database's contents and settings can be subsequently saved by choosing link 1334. Accordingly, the graphical user interface 1320 provides the operator with a selection of tools for selecting, formatting and saving data assessment files.

The graphical user interfaces presented herein are merely exemplary of interfaces that may be used to assist the user or expert operator in communication with the robotic apparatus and associated sensors. The interfaces may be modified according to the needs of both the user and the expert operator. In addition, once the operator has selected a file for review and analysis, they may use different tools for conducting the analysis of the progress of the patient.

Advantages Over the Prior Art

The robotic apparatus of the preferred embodiment enables a user to operate the robot through biometric wearable sensors and/or activating controls on a console. One of the advantages of the apparatus is its flexibility, which is manifested in many forms. First, the user inputs can come from any type of sensor capable of sensing biometric signals measuring position, velocity, acceleration, force, auditory signals, electrical activity, temperature, scent, optical signals, or electromagnetic radiation emanating from a sensor located anywhere on the user or on a console. Second, the relationship between the sensor inputs and the robot's actuators can be any combination of sensors necessary to activate any combination of actuators. One or more sensor can be mapped to a single actuator, and one or more actuator outputs can be mapped to a single sensor input. The sensor input to actuator output relationships can be further modified to adjust the threshold and gain settings.

The third degree of flexibility is the manner in which the user interacts with the robot. The user can interact with the robot by activating the sensor inputs in real-time mode and/or using play and record capabilities. In addition, the user and the robot can be engaged within an interactive game or story. During an interactive game or story, the mapping and threshold settings between inputs and robotic outputs can be dynamic in nature, so that the manner in which the robot is controlled changes within the course and context of the game or story.

The fourth degree of flexibility is due to the wireless connectivity between the robot and its inputs. Since the user is not physically attached to the robot, there is a great degree of freedom of movement between the user and the robot. In addition, the robot, the wearable sensors, and/or the controlling console can be communicating near each other, over a local wireless communication network, or distant from each other, over a long-distance communication network such as the Internet. This flexibility greatly enhances the number of alternative embodiments, for example; allowing users to interact with a remote robot; multiple users from different locations to interact with single or multiple robots at one location; and, allowing an operator to monitor a user's interaction with a robot, either in real-time or post-session.

The fifth degree of flexibility is provided by the ability to update the content of interactive games and stories. The user can create or modify games or stories and/or download games and/or stories created by other authors, across a communication network The means for new content sustains the novelty of the robotic apparatus, providing continual interest value that is critical for educational, therapeutic, motivational, and entertainment applications.

The ability to save data recorded from sessions with the robotic apparatus enhances the system's capabilities for educational and therapeutic use. Data can be viewed in real-time, either locally or remotely, in whatever presentation is chosen by the operator. In addition, data can be saved and later viewed in a presentation chosen by the operator. Furthermore, data can be stored in a database for convenient monitoring of a user's performance with the robotic system over the course of time.

Alternative Embodiments

It will be appreciated that, although specific embodiments of the invention have been described herein for purposes of illustration, various modifications may be made without departing from the spirit and scope of the invention. In particular, the robotic apparatus in communication with the wireless sensors is shown as a physical apparatus with assemblies controlled by motors and actuators. However, the robotic assembly may also be in a virtual form. In this embodiment, the robotic assembly would be present on a monitor and the user would control the various components of the robot on the monitor. The input of various sensors would cause the virtual robotic apparatus to move different assemblies or to move in specific directions in the virtual environment. For example, the robotic apparatus can be displayed on a computer monitor in an interactive game wherein the movement of the sensors may allow the user to control the different aspects of the game.

In the physical form of the robotic apparatus, the apparatus includes motors for controlling movement of the various assemblies, as well as sensors for communicating with the motors. Both the sensors and motors may come in a variety of forms, including digital and analog. For example, the sensor or network of sensors may be in a glove or a similar component. The glove may include sensors for sensing movement of different fingers as well as the hand and/or wrist. The robotic apparatus may be designed to incorporate a computer. The computer may be in a console, or it may be in communication with a communication port of a console, or it may be a part of the robotic apparatus itself. In any of these embodiments, the computer may be connected to an external personal computer and/or server to enable downloading of files from the apparatus to the external computer and/or server, uploading of files to the apparatus, and general control of the apparatus from a remote location both in real-time mode control as well as for a delayed assessment of sensor data. The user may also be located remotely to the robot controlling the robot through a networked console. The flexible network capabilities of the robotic apparatus will be particularly valuable for tele-health applications where the caregiver and the patient are in different locations.

The robotic apparatus may also be configured as multiple robots with multiple users and multiple consoles and any number of combinations thereof. Variations of this embodiment would be to incorporate a multitude of environmental and biometric sensors on the apparatus including, but not limited to video, ultrasound, infrared, pressure sensors, and auditory. The robotic apparatus can be configured with advanced behaviors, which may be autonomous, such as the ability to sense and avoid obstacles; the ability to sense and follow the user; or the ability to detect and determine the location of the robot with respect to the operating environment. Accordingly, the scope of protection of this invention is limited only by the following claims and their equivalents.

We claim:

1. A robotic apparatus comprising:
   (a) a controller adapted to process a signal to an actuator;
   (b) a dynamic feedback control system between a sensor and said actuator, said control system having said sensor to sense input and to communicate a wireless signal of said sensor with said actuator;
   (c) said actuator adapted to receive said signal and to actuate a robotic part in response to said input exceeding a defined threshold;
   (d) wherein said sensor is a biometric sensor with input selected from the group consisting of: position, velocity, acceleration, force, and auditory.

2. The apparatus of claim 1, further comprising said robot having a sensor.

3. The apparatus of claim 1, wherein said biometric sensor input is selected from the group consisting of: thermal, electrical, optical, scent, video, ultrasound, infra red, pressure, and electromagnetic radiation.

4. The apparatus of claim 2, wherein said robot sensor is a biometric sensor whose input is selected from the group consisting of: thermal, electrical, and optical.

5. The apparatus of claim 1, wherein said input of said user is physical.

6. The apparatus of claim 1, wherein said sensor is secured to said user.

7. The apparatus of claim 1, wherein said sensor is secured to a console.

8. The apparatus of claim 1, wherein said robotic part is selected from the group consisting of: an arm assembly, a leg assembly, a head assembly, facial components, any actuator in communication with the controller, and combinations thereof.

9. The apparatus of claim 1, further comprising a computer to store data received from said sensor.

10. The apparatus of claim 9, wherein said computer is mounted in a location selected from the group consisting of: internal to said robotic part, internal to said sensor, external to said robotic part, and combinations thereof.

11. The apparatus of claim 1, further comprising an operator interface to modify configuration of said robotic part.

12. The apparatus of claim 11, wherein said operator interface includes a menu to select an interactive mode of operation between said robotic part and said user.

13. The apparatus of claim 11, wherein said operator interface allows an operator to evaluate said user input.

14. The apparatus of claim 11, wherein said operator interface is accessible from a location remote from said robotic part and said user.

15. The apparatus of claim 11, wherein said operator interface allows an operator to program an unique interactive mode of operation.

16. The apparatus of claim 1, wherein said robotic part is selected from the group consisting of: a physical apparatus, a virtual apparatus, and combinations thereof.

17. A method for controlling a robotic apparatus comprising:
(a) reading biometric sensor data in communication with said apparatus;
(b) processing said sensor data;
(c) transmitting said sensor data over a wireless connection from said sensor to a receiver in communication with said apparatus;
(d) parsing said sensor data; and
(e) activating an actuator of said robot in response to said parsed data; and
(f) interacting with said apparatus in a dynamic feedback control system,
(g) wherein the step of processing said sensor data includes functions selected from the group consisting of: analog to digital converting, compressing said data, mapping said data, thresholding said data, and pattern recognition.

18. The method of claim 17, further comprising the step of providing feedback from said apparatus to a user.

19. The method of claim 18, wherein said feedback is biometric feedback selected from the group consisting of: visual, tactile, auditory, and combinations thereof.

20. The method of claim 17, wherein the step of processing said sensor data includes processing physical input signals.

21. The method of claim 17, further comprising the step of directly transmitting said sensor data to said apparatus for controlling said actuator of said apparatus in real-time.

22. The method of claim 17, wherein the step of processing said sensor data includes functions selected from the group consisting of: filtering said data, and encrypting said data.

23. The method of claim 17, wherein the step of parsing said sensor data includes functions selected from the group consisting of: analog to digital converting, de-encrypting said data, de-compressing said data, pattern recognition, mapping said data, filtering said data, thresholding said data, and combinations thereof.

24. The method of claim 17, further comprising the step of recording said sensor data.

25. The method of claim 24, further comprising the step of retrieving said recorded sensor data and playing said data for activating select parts of said apparatus associated with said data.

26. The method of claim 24, wherein the step of recording said sensor data includes saving said data in a medium in communication with an apparatus selected from the group consisting of: said sensor, said apparatus, a remote console, and combinations thereof.

27. The method of claim 24, further comprising the step of accessing said sensor data from a remote location for evaluation of said data.

28. The method of claim 17, further comprising the step of providing interactive communication between said sensor and said apparatus.

29. The method of claim 17, further comprising the step of modifying configuration of said apparatus through an operator interface in wireless communication with said apparatus.

30. The method of claim 29, wherein the step of modifying configuration of said apparatus includes modifications selected from the group consisting of: mapping of said sensor data from said operator interface to said apparatus, modifying thresholds and gains, selecting a platform for interactive communication attributes of said apparatus, and combinations thereof.

31. The method of claim 17, further comprising the step of connecting said apparatus to a communication network.

32. The method of claim 17, further comprising the step of connecting a remote console to a communication network.

33. An article comprising:
a computer-readable signal-bearing medium;
means in the medium for sending data over a wireless connection;
means in the medium for communicating activation of a signal in a remote robotic apparatus;
means in the medium for remotely setting configuration parameters of a biometric sensor and an actuator of said robotic apparatus;
means in the medium for providing dynamic interaction between said robotic apparatus and a user in communication with said robotic apparatus,
wherein said configuration parameters are selected from the group consisting of mapping, calibration, thresholding and gains.

34. The article of claim 33, wherein the medium is selected from the group consisting of: a recordable data storage medium, a modulated carrier signal, and combinations thereof.

35. The article of claim 33, wherein said means for communicating activation of a signal is a communication protocol.

36. The article of claim 33, wherein said means for remotely setting configuration parameters is a graphical user interface.

37. The article of claim 33, wherein said configuration parameters are selected from the group consisting of: mapping, calibration, thresholding and gains, and combinations thereof.

38. The article of claim 33, further comprising conducting assessment of signal data in said medium.

39. The article of claim 38, wherein said assessment is selected from a group consisting of: real-time and delayed.

40. The article of claim 33, further comprising providing remote interaction between an operator to said robotic apparatus in real-time in said medium.

41. The article of claim 40, wherein said remote interaction includes retrieving a set of instructions to provide interactive communication between said robotic apparatus and said user.

42. The article of claim 33, further comprising saving said data in said medium.

43. The article of claim 33, further comprising transmitting said data to a computer remote from said robotic apparatus.

44. The article of claim 43, further comprising conducting assessment of said data in said medium.

45. The article of claim 44, wherein said assessment is selected from a group consisting of: real-time local, real-time remote, manual, and embedded.

46. A wireless signal communication system comprising:
   (a) a sensor in remote communication with an actuator;
   (b) a power control module;
   (c) a transceiver;
   (d) a central processing unit; and
   (e) a dynamic control system between said sensor and said actuator adapted to enable control of said actuator in response to feedback communicated to said sensor,
   (f) wherein said sensor is a biometric sensor whose input is selected from a group consisting of: position, velocity, acceleration, force, and auditory.

47. The system of claim 46, wherein said transceiver and said central processing unit are adapted to receive and process sensor data and to transmit said data to said actuator.

48. The system of claim 46, further comprising a plurality of wireless sensors in communication with a single central processing unit.

49. The system of claim 48, wherein said plurality of sensors are physically connected.

50. The system of claim 46, further comprising a plurality of central processing units with each unit comprising a plurality of connected sensors.

51. The system of claim 46, wherein said actuator is selected from the group consisting of: virtual and physical, and combinations thereof.

52. The system of claim 46, wherein said transceiver and said central processing unit are connected to a communication network.

53. The system of claim 46, wherein said biometric sensor input is selected from a group consisting of: thermal, electrical, optical, scent, infra red, ultrasound, video, pressure, and electromagnetic radiation.

54. A method for controlling a robotic apparatus comprising:
   (a) reading biometric sensor data in communication with said apparatus;
   (b) processing said sensor data;
   (c) transmitting said sensor data to a receiver in communication with said apparatus;
   (d) parsing said sensor data;
   (e) activating an actuator of said robot in response to said parsed data;
   (f) interacting with said apparatus in a dynamic feedback control system;
   (g) wherein the step of interacting with said apparatus in a dynamic feedback control system is initiated by said robotic apparatus; and
   (h) wherein the step of processing said sensor data includes functions selected from the group consisting of: analog to digital converting, compressing said data, mapping said data, thresholding said data, and pattern recognition.

* * * * *